(12) United States Patent
Strikovski et al.

(10) Patent No.: US 9,651,369 B1
(45) Date of Patent: May 16, 2017

(54) METHOD AND SYSTEM FOR IN-SITU DETERMINATION OF A CHEMICAL COMPOSITION OF FILMS DURING GROWTH PROCESS

(71) Applicant: NEOCERA, LLC, Beltsville, MD (US)

(72) Inventors: Mikhail Strikovski, Gaithersburg, MD (US); Jeonggoo Kim, Laurel, MD (US); Solomon Kolagani, Ellicott City, MD (US); Steven L. Garrahan, Odessa, FL (US)

(73) Assignee: Neocera, LLC, Beltsville, MD (US)

( * ) Notice: Subject to any disclaimer, the term of this patent is extended or adjusted under 35 U.S.C. 154(b) by 0 days.

(21) Appl. No.: 15/165,519

(22) Filed: May 26, 2016

Related U.S. Application Data

(60) Provisional application No. 62/139,412, filed on Mar. 27, 2015.

(51) Int. Cl.
| | |
|---|---|
| *G01B 15/02* | (2006.01) |
| *G01N 23/225* | (2006.01) |
| *C23C 16/48* | (2006.01) |

(52) U.S. Cl.
CPC .......... *G01B 15/02* (2013.01); *C23C 16/484* (2013.01); *G01N 23/2252* (2013.01)

(58) Field of Classification Search
CPC ... G01B 15/02; C23C 16/484; G01N 23/2252
See application file for complete search history.

(56) References Cited

U.S. PATENT DOCUMENTS

| | | | | |
|---|---|---|---|---|
| 2009/0074137 A1* | 3/2009 | Agnihotri | .............. | G01B 15/02 378/50 |
| 2013/0202084 A1* | 8/2013 | Piorek | .................. | G01N 23/223 378/45 |
| 2014/0119513 A1* | 5/2014 | Kim | ..................... | G01N 23/223 378/89 |

OTHER PUBLICATIONS

"Scanning electron microscopy and X-ray microanalysis", J. Goldstein, D. Newbury, D. Joy, C. Lyman, P. Echlin, E. Lifshin, L. Sawyer, J. Michael, 3-rd edition, Springer, 2003, Ch. 9.

"Quantification in X-Ray Fluorescence Spectrometry", Rafal Sitko, Beata Zawisza, Spectrochimica Acta, Part B, Atomic Spectroscopy 64(11-12), pp. 1161-1172, Oct. 2009.

(Continued)

*Primary Examiner* — Nicole Ippolito
*Assistant Examiner* — Sean Luck
(74) *Attorney, Agent, or Firm* — Rosenberg, Klein & Lee

(57) ABSTRACT

System and method for determining the composition of deposited thin films by acquiring multiple sequential X-ray spectra for a film of interest during the deposition process as the film thickness increases, computing intensities of peaks found in the X-ray spectra corresponding to elements present in the film material, followed by computing, for each pair of elements, ratios of corresponding peak intensities, graphing the intensities and ratios against a parameter correlated to the film thickness, and applying a physically meaningful function to the graphed data for best fitting the data down to a ratio $R_{A/B}(0)$ for each pair of the elements for a virtual film of zero thickness. Elemental concentrations ratio for each pair of elements is subsequently computed as a product of $R_{A/B}(0)$ and a factor which is specific for the pair of elements, constant for the instrument as set up, and independent of elements concentrations, and of film thickness.

20 Claims, 14 Drawing Sheets

(56) References Cited

OTHER PUBLICATIONS

"Performing elemental microanalysis with high accuracy and high precision by scanning electron microscopy/silicon drift detector energy-dispersive X-ray spectrometry (SEM/SDD-EDS)", Dale. E. Newbury, Nicholas W.M. Ritchie, J. Mater. Sci. (2015), 50:493-518. DOI10.1007/s10853-014-8685-2.
"The quantitative analysis of thin specimens: a review of progress from the Cliff-Lorimer to the new ζ-factor methods", M. Watanabe, D.B. Williams, Journal of Microscopy, vol. 221, Pt.2, Feb. 2006, pp. 89-109.
Electron beam induced x-ray emission: An in situ probe for composition determination during molecular beam epitaxy growth Joseph G. Pellegrino, John Armstrong, Jeremiah Lowney, Barbara DiCamillo and Joseph C. Woicik, Appl. Phys. Left. 73, 3580 (1998).
Massachusetts Institute of Technology, Electron Microprobe Facility, "Electron Microprobe Analysis", Course 12.141, Lecture Notes by Dr. N. Chatterjee.
Oxford Instruments, "EDS in the TEM explained".
Jeol, XM-17330/27330, "Basic Software/Quantitative analysis program".
DTSA-II, multiplatform software package for quantitative x-ray microanalysis.
XRS-FP2, Quantitative XRF Analysis Software, AMPTEK.
"A thin film approach to engineering functionality into oxides". DarrellG. Schlom, Long-Qing Chen, Xiaoqing Pan, Andreas Schmehl, and Mark A. Zurbuchen, J. Am. Ceram. Soc. 91; [8] 2429-2454 (2008).
X-ray Detector Selection Guide, Amptek.

\* cited by examiner

METHOD AND SYSTEM FOR IN-SITU DETERMINATION OF A CHEMICAL COMPOSITION OF FILMS DURING GROWTH PROCESS

REFERENCE TO THE RELATED PATENT APPLICATIONS

This Utility Patent Application is based on the Provisional Patent Application No. 62/139,412 filed on 27 Mar. 2015.

FIELD OF INVENTION

The present invention relates to quality control of thin films, and, in particular, to a method and a system for determination of parameters of thin films.

More in particular, the present invention relates to a method and a system for real-time in-situ determination of the chemical composition of multi-elemental films during deposition process.

In overall concept, the present invention is directed to determination of a chemical composition of thin films based on an analysis of multiple X-ray spectra dynamically acquired during thin film growth.

The present invention is also directed to a system and method for in-situ, real-time, determination of a chemical composition of thin films by applying dynamic spectrometry principles to compute, from multiple X-ray spectra acquired during the thin films growth, a ratio value of intensities of elemental lines corresponding to the films' zero thickness condition which is directly related to the films elemental composition.

BACKGROUND OF THE INVENTION

Chemical composition of multi-elemental thin films grown on a substrate critically affects the films' electrical, optical, as well as mechanical and other properties which are important for the films' practical applications. The chemical composition may be defined as a set of relative values, i.e., atomic concentrations of chemical elements present in a film of interest with respect to a concentration of one of the chemical elements in the film.

A spectroscopic approach has been developed in the industry to obtain a chemical composition by analyzing relative intensities of characteristic X-ray lines corresponding to the elements present in a material under study. Some examples of related spectroscopic techniques include the Energy Dispersive X-ray Spectrometry (EDS) and the X-ray Fluorescence (XRF). The EDS technique is based on the analysis of X-rays emitted from a surface exposed to an impact of an energetic electron beam. The XRF technique utilizes an X-ray source to excite the characteristic radiation.

Shortcomings of the existing X-rays spectrometry techniques for the quantitative composition analysis include the inability to obtain a direct proportionality between the measured intensity of an elemental X-ray line and the concentration of a corresponding chemical element.

Specifically, for the EDS technique, the reasons for such shortcomings are the complex interactions between the electron beam and the material under study, as well as between the X-ray and the material under study. The core of such complexity is the parametric nature of the problem, i.e., unknown parameters to be determined are part of the very equations and factors describing those interactions. This is aggravated by multiple compositionally dependent inter-element effects (for example, dependence of the intensity of one element line on the concentration of another element) as presented in "*Scanning electron microscopy and X-ray microanalysis*", J. Goldstein, et al., Ch. 9-10, $3^{rd}$ edition, Springer, 2003; and Massachusetts Institute of Technology, Electron Microprobe Facility, "Electron Microprobe Analysis", Course 12.141, Lecture Notes by Dr. N. Chatterjee.

A number of models have been developed for calculation of an X-ray profile generated by decelerating electrons. However, these models are not satisfactory due to the fact that the spatial distribution of X-rays generation density inside films lacks uniformity and depends on elemental concentrations itself, as well as due to their inability for precise determination of atomic factors needed for the calculations.

Another difficulty of the chemical composition determination, is that, once generated in the volume of the material under study, X-rays experience absorption along their path to the film surface. A degree of such absorption, and thus the intensity of X-rays registered by an outside sensor, is, similar to the spatial distribution, parametric due to its dependency on the material composition.

A technique has been developed in the industry for the chemical composition determination based on utilization of standardized material samples ("*Quantitative X-ray fluorescence analysis of samples of less than infinite thickness: difficulties and possibilities*", Rafal Sitko, et al., Spectrochimica Acta, Part B, Atomic Spectroscopy 64(11-12), pp. 1161-1172, October 2009; and "*Electron beam induced x-ray emission: An in situ probe for composition determination during molecular beam epitaxy growth*" Joseph G. Pellegrino, et al., Appl. Phys. Lett. 73, 3580 (1998)). In this approach, in order to link the emitted X-ray lines intensities to elemental concentrations, multiple calibrations are performed on bulk material samples of a known composition. The calibrations are processed by specific software to obtain the composition. The computations in this material standard based approach are overly complicated when applied to analyzing multi-elements materials (films) which contain a wide variety of elements. In addition, some calibration techniques require extra measurements to be performed with varying energies or with varying angles of an incident electron beam.

Another theoretical approach for determining films' chemical compositions relies on computations of multiple "matrix corrections" (ZAF) factors, which are applied to measured X-ray line intensities ("*The quantitative analysis of thin specimens: a review of progress from the Cliff-Lorimer to the new ζ-factor methods*", M. Watanabe, D. B. Williams, Journal of Microscopy, vol. 221, Pt.2, February 2006, pp. 89-109; Oxford Instruments, "EDS for TEM explained"; and JEOL, XM-17330/27330, "Basic Software/ Quantitative analysis program"). The computations take into account effects of chemical elements' atomic number, absorption, fluorescence, etc. Due to the complexity of interrelations between the material parameters and material interaction with the electron beam and X-rays, corrections are calculated based on numerous models which require an extensive database of X-ray parameters. Some values of elements and the material's factors needed for these computations often are not known accurately, or not applicable directly to experimental conditions.

For thin films, the situation is more complex due to the fact that the intensity of the X-ray emitted by a film depends on its thickness.

The knowledge of a film's thickness is also necessary for the accurate composition quantification of the film, which requires another layer of additional measurements and/or theoretical modeling. Moreover, not only the geometrical thickness of the film under study, but also topological difference between the standard samples and the real material surface (roughness, micro-particles, etc.) can strongly affect the measurements result.

The shortcomings of the existing techniques may contribute to somewhat "insufficient" analytical performance of the EDS which is regarded as only a "semi-quantitative" technique, due to the fact that the chemical composition measured through the EDS approach for thin films' chemical composition determination generally severely deviate from a true chemical composition.

Another disadvantage of the typical electron probe microanalysis systems is the electron beam positioning at 90° relative to the film surface. This arrangement is deficient in that the generation of X-rays occurs mostly inside the substrate, but not in the thin films of interest. Typical penetration ranges of energetic electrons in solids is approximately several microns, which is larger than ≤100 nm thickness of the films of interest. If electrons are incident on the film at a large angle to the surface (for example, perpendicular to the surface), they travel inside the film a small fraction of their total penetration range, and the probability of X-rays generation for the film's elements is low.

Additionally, a small incidence angle of the electron beam is not desired due to scattering of a large number of the beam electrons from the surface for incidence angles below 3 degrees, resulting in that the scattered beam electrons are prevented from contributing to the X-rays generation.

Thus, a long-lasting need exists in the thin films manufacturing to address the aforementioned deficiencies of thin films composition analysis, and to obviate deficiencies of the existing systems and approaches by relying neither on the standard bulk samples calibrations, theoretical modeling, nor on prior knowledge of films' thicknesses.

In addition it is desirable to provide a technique for the X-ray analysis where the beam electrons contribute into the X-ray generation in the most efficient manner.

SUMMARY OF THE INVENTION

It is, therefore, an object of the present invention to provide a dynamic spectrometry technique which does not require knowledge of a film's thickness, and which is based on acquisition and analysis of multiple X-ray spectra to determine a parameter, i.e., ratio R(0) of elemental lines intensities at a zero film thickness which is directly related to and is unique to the film elemental composition and does not depend on the film thickness.

Another object of the present method and system is to determine in-situ (during the film growth) a multi-elemental film's composition without breaking vacuum or removing films from the deposition chamber as the film thickness increases during the deposition process.

An additional object of the present invention is to provide a routine for spectra acquisition and analysis, which includes collection of multiple spectra as film thickness increases, beginning with an initial stage of the deposition process when a film's thickness is zero, where each X-ray spectrum is acquired at a different film thickness, and where no knowledge of the film's thickness values is needed for determining the film's chemical composition.

It is also an object of the present technique to provide a method which follows the dynamics of the Ratio of intensities change as the thickness of the film changes, and which analyzes each spectrum collected at a different thickness of the film (during the deposition process) in order to extract relative radiation intensities of elemental characteristic X-rays. The computations do not require knowledge of the film thickness, or the deposition rate, but uses a parameter which is related to or serves as a measure of the thickness of films under study (for example, a number of deposition laser pulses, deposition time, etc.).

It is a further object of the present invention to provide a technique which applies an analytical algorithm to the measured Ratios (R) of intensities $J_A$ and $J_B$ of pairs of elements A and B, to result in a value of a unique zero-film-thickness ratio parameter, $R_{A/B}(0)$, which is directly proportional to the relative concentration of a pair of elements in a film under study (i.e., to the film composition), and independent of the film thickness. By utilizing the R(0) value in the composition computations, the subject system and method eliminates major obstacles of the quantitative X-ray spectrometry for composition analysis of films (i.e., corrections needed to account for non-uniformity of electron-generated X-rays and their absorption in films of different thickness). The subject system and method uses a procedure applied to a set of spectra acquired to identify R(0) value, and converts the R(0) value into the film composition.

Another object of the subject method is to deviate from using film or bulk material standard samples to calibrate an X-ray spectrometer for elemental sensitivities or theoretical calculations of parameters for quantification, and to provide a self-calibration routine based on a single sample, the composition of which is quantified by an independent technique.

Even though not required for films composition determination, the subject method also is capable of measurements of a film thickness in real-time, i.e., during the deposition process, based on monitoring of dynamic changes in the intensity of an X-ray line emitted by a substrate material. As the film thickness on the substrate increases, the intensity of the X-ray line decreases from its maximum (at the zero film thickness) due to decrease in the amount of X-rays generated in the substrate as well as the absorption of those X-rays in their path through the film. In this process, the degree of reduction (decay) of the X-line intensity can be directly linked to the film thickness at a specific time. The subject method uses the characteristic length for the decay (a physical constant for a given pair of the substrate-film materials), which is computed once by a self-calibration procedure, to be subsequently used to obtain the real-time film thickness and the average deposition rate at any moment during the film growth process.

In addition, the subject method provides a technique to evaluate compositions of multiple films deposited in a layered manner. If a superpositioned film contains new elements which are different from the elements in the underlying films, new characteristic X-ray lines appear in the emitted spectrum, and the intensities of the new X-ray lines increase along with the superpositioned film thickness increase. Dynamics of the new X-ray lines intensities can be analyzed in the same way as for a single film on the substrate, in order to determine the composition of the new film.

In one aspect, the present invention is a method for in-situ determination of chemical composition of films during deposition process. The subject method includes:

(a) positioning an underlying structure in a deposition chamber, and bombarding a predetermined area on said underlying structure with an electron beam incident on a surface of the underlying structure at a first predetermined angle;

(b) operatively coupling an X-ray spectrum acquisition sub-system to the surface of the underlying structure;

(c) acquiring, by said X-ray spectrum acquisition sub-system, a "zero-film" X-ray spectrum produced by the underlying structure upon exposure to the electron beams prior to deposition of a film of interest on the underlying structure;

(d) initiating a deposition process to deposit a material containing at least two elements A and B for the film of interest on the underlying structure, wherein the deposition process is performed in a plurality of sequential predetermined stages, each stage for deposition of a partial thickness of the film of interest; and for each of the deposition stages:

(e) acquiring, by the X-ray spectrum acquisition system, a respective X-ray spectrum emitted from the film of interest for each stage of the deposition process;

(f) analyzing the respective X-ray spectrum relative to the "zero-film" X-ray spectrum to determine at least two X-ray peaks present, where each of at least two X-ray peaks corresponds to a respective element of the at least two elements A and B of the material of the film of interest, (g) computing intensities $J_A(N)$ and $J_B(N)$ of the peaks where N is a parameter corresponding to a thickness of said film of interest formed during each stage of the deposition process, (h) computing a ratio $R_{A/B}(N)$ of the intensities $J_A$ and $J_B(N)$, and (i) computing a ratio $R_{A/B}(0)$ for a virtual film of substantially zero thickness for the two elements A and B by applying a best fitting function across the $J_A(N)$, $J_B(N)$, and $R_{A/B}(N)$ in at least one stage, and (j) computing a ratio of concentrations $C_A/C_B$ for the elements A and B as a product of the value of the $R_{A/B}(0)$ and a relative sensitivity factor $K_{A/B}$, which is an instrumental factor constant for a pair of elements A and B, which is independent of their relative concentration and of the film thickness.

Steps (d)-(j) for the plurality of stages of the deposition process are repeated until the deposition process is complete or sufficient data for determining the film composition is obtained.

The subject method allows computation of the chemical composition of a film on a substrate, as well as films deposited on the top of a previously deposited film. Thus, the underlying structure is either a substrate for the film of interest deposition, or a film-on-substrate structure underlying the film of interest.

Subsequent to the step (c), the logic underlying the method determines "zero-film" correction spectrum data corresponding to contribution of unwanted residual elements, and in the step (f), performs a correction routine by applying the correction spectrum data to the X-ray spectrum to subtract X-ray counts produced by the unwanted residual elements for the respective X-ray spectrum acquired during each stage of the deposition process.

The deposition procedure may be interrupted for a time period sufficient for each stage's data acquisition and processing if the speed of the spectrum acquisition is lower than the speed of the film increase. Otherwise, the stages' data deposition/acquisition/processing can follow each other without time break.

The relative sensitivity factor $K_{A/B}$ for the two elements A and B is determined prior to the step (j) through the steps of:

depositing a calibration film containing at least the elements A and B, and applying the steps (c)-(j) for measuring of the $R_{A/B}(0)$ of the calibration film, determining the composition $C_A/C_B$ of the calibration film by an independent technique (such as, for example, Rutherford backscattering, or mass-spectrometry), and subsequent to determination of the $R_{A/B}(0)$ and $C_A/C_B$ for the calibration film, calculating the relative sensitivity factor $K_{A/B}=(C_A/C_B)/R_{A/B}(0)$.

The parameter corresponding to a thickness of the film of interest includes a number of laser pulses or a time of deposition, or any other parameter which may serve as a measure of the film thickness.

If the film deposition material includes more than two elements, i.e., at least elements A, B, and C, the method further includes:

for each stage of the deposition technique, in the step (g), computing values of peak intensities J(N) of elemental lines corresponding to the elements A, B, and C, graphing the intensities J(N) of each elemental peak against the thickness related parameter N, computing ratios $R_{A/C}(N)$, $R_{B/C}(N)$ of intensities $J_A(N)$, $J_B(N)$, of each element A, B to the intensity $J_C(N)$ of the element C, curve-fitting said J(N) and R(N) for the elements A, B, and C across data points available, and for each element A and B, the curve-fitting of $R_{A/C}(N)$ and $R_{B/C}(N)$ down to respective $R_{A/C}(0)$ and $R_{B/C}(0)$ values of the ratios.

The subject method allows determination of a thickness of the film of interest as a function of reduction of the intensity Js of at least one elemental peak corresponding to a material of the underlying structure found at the "zero-film" X-ray spectrum through the steps of:

obtaining in step (c), intensity Js(0) of at least one elemental peak of the underlying structure (for example, the substrate) material found in "zero-film" X-ray spectrum;

computing a normalized intensity Js(N)/Js(0) of the elemental peak after the film thickness related parameter N has been applied during the deposition procedure, calibrating the normalized intensity against a calibration film having a known thickness for a given pair of substrate element-film material, and applying the calibration results to the measured normalized value Js(N)/Js(0) to calculate the film of interest thickness in real-time.

Another object of the present invention is to provide an apparatus configured with an optimized angle of the electron beam incidence on the film surface during X-ray acquisition, to obviate disadvantages of the common electron probe microanalysis setups.

In the subject system, the electron beam is positioned to be incident on the film surface at a small glancing angle, so that the energetic electrons spend a greater fraction of their travel length (when compared to the perpendicular arrangement) within the film. This results in an increased efficiency of the X-ray radiation generation from the film elements. The electron beam incidence angle of 5 degree has been determined to be an optimum arrangement for the purpose of the subject system and method.

It is an additional object of the subject system to ensure that acquired X-rays originate from a newly-deposited film on the substrate rather than from parts of components of assembly nearby or from materials of previous depositions.

Furthermore, an additional object of the subject apparatus is to provide a mechanism for evaluation of the film composition at multiple locations on the film, i.e., to obtain a "map" of film compositions.

In another aspect, the subject invention relates to a system for in-situ determination of chemical composition of films during a deposition process which includes a deposition chamber, a substrate positioned within the deposition chamber, and a source of deposition material for deposition on a surface of the substrate to grow a film of interest.

An electron beam is directed to be incident on the surface of the film of interest at a first predetermined angle, and at least one X-ray sensor is positioned at a second predetermined angle relative to the surface to collect X-rays emitted therefrom.

A spectra acquisition sub-system is operatively coupled to the X-ray sensor and is configured to form a respective X-ray spectrum from X-rays counts collected by the X-ray sensor during each of a plurality of stages of the deposition and acquisition process.

A spectra processing sub-system is operatively coupled to the X-ray spectra acquisition sub-system and is configured to analyze the respective X-ray spectrum to determine at least two X-ray peaks present. Each of the X-ray peaks corresponds to a respective element of at least two elements A and B of the deposition material of the film of interest. The spectra processing sub-system computes intensities $J_A(N)$ and $J_B(N)$ of the peaks, and computes a ratio $R_{A/B}(N)$ between the intensities $J_A(N)$ and $J_B(N)$.

A composition computation sub-system is operatively coupled to the spectra processing sub-system and is configured to compute a ratio $R_{A/B}(0)$ for a virtual film of substantially zero thickness for the elements A and B by applying a best fitting function across the $J_A(N)$, $J_B(N)$ and $R_{A/B}(N)$ in each stage, and a ratio of concentrations $C_A/C_B$ for each two elements A and B which is computed as a product of the value of the $R_{A/B}(0)$ and a relative sensitivity factor $K_{A/B}$ which is an instrumental factor for the elements A and B pair. The factor $K_{A/B}$ is a constant that is independent of the elements' relative concentration in films, and of films thickness.

The subject system further includes a control unit operatively coupled to the source of electron beam source of deposition material, an X-ray sensor, and the X-ray acquisition sub-system, spectra processing sub-system and composition computing sub-system to control the deposition process, the X-ray emission, the first and second predetermined angles, and the X-ray acquisition and processing routines, for acquiring the X-ray spectra for a plurality of subsequent deposition process stages, and to process said X-ray spectra for each said deposition stage integrally until the deposition process is completed.

In the subject system, a user interface is operatively coupled to the control unit, and the X-ray spectra processing and composition computing sub-systems.

The system further includes X-ray gate shields disposed between the substrate or the film of interest and the X-ray sensor. The gate shields are configured to be positioned with a controllable first distance therebetween and a controllable second distance relative to the surface of the substrate or the film of interest to prevent detection of unwanted emitted X-rays by the X-ray sensor.

The subject system further includes an interrogating mechanism for acquiring X-ray spectra from a plurality of areas on the surface of the film of interest. The interrogating mechanism includes a screen formed with a plurality of screen windows disposed between the film of interest and the X-ray sensor, and a selector shield formed with a selector window and disposed between the screen and the X-ray sensor. A relative disposition between the screen and the selector shield is controlled to align the selector window with a respective one of the screen windows corresponding to an area of interest on the film of interest. The film of interest is controllably displaceable relative to the electron beam.

The system further includes a collimator assembly mounted at an input of the X-ray sensor and configured to control the field-of-view, and further includes a protector structure positioned in front of the X-ray sensor to prevent contamination of the window of the X-ray sensor.

These and other objects and advantages of the present system and method will be apparent from reading the following detailed description of the invention in conjunction with the accompanying Patent Drawings Figures.

DETAILED DESCRIPTION OF THE PREFERRED EMBODIMENT(S)

Chemical composition of film is a dimensionless number defined as an atomic concentration of one element relative to an atomic concentration of another element. Intensities of X-ray lines produced by the elements when bombarded by electrons are proportional to concentrations of the elements. This phenomena underlies the subject approach for finding the composition number in which a dimensionless number (i.e., the ratio R of intensities of elemental peaks produced by elements) is measured, and a proportionality factor is applied to the numbers.

Figure 1:
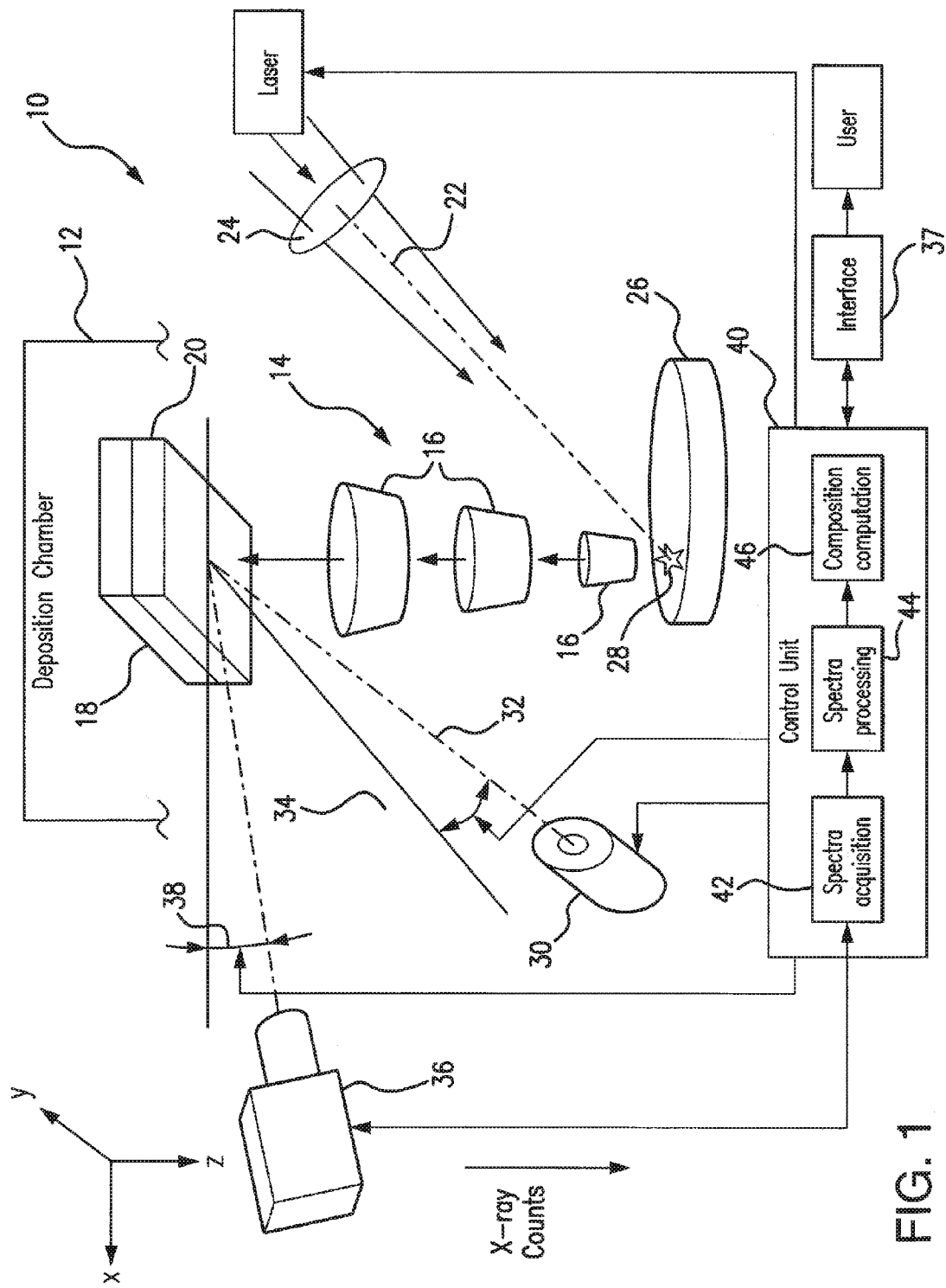
FIG. 1 is a schematic representation of the subject system adapted for the Pulsed Laser Deposition film growth technique.

Referring to FIG. 1, the subject system 10, although being able to use various film deposition techniques, as an example (but not to limit the scope of the subject invention protection) is presented herein as using the pulsed laser deposition (PLD) technique as a film growth technique, which is performed in a chemical PLD chamber 12, also referred to herein as a deposition chamber. In the system 10, a deposition material 14 arrives in pulsed portions 16 to a substrate 18.

The pulsed laser deposition technique is performed to deliver the material 14 to the substrate 18 to form at least one film 20.

The laser pulse power 22 is focused with lens 24 onto the surface of the material source tablet 26 (material target). With each pulse applied, some amount 16 of the target material 14 is ejected from the focus point 28 on the material target 26, and the thickness of the film 20 increases. In the PLD, the total thickness of the film 20 is proportional to the number N of deposition pulses executed.

Energetic (20-30 keV) electrons (electron beam) 32 (created by the e-beam source 30) are incident on the substrate 18 (or on the deposited film 20) at a small (for example, 5 degree) glancing angle 34 (selected in accordance with the principles detailed in further paragraphs). The electron beam 32 is focused (to <1 mm diameter) to limit the beam footprint on the surface of the film 20 preferably to less than the deposition area of the film 20.

The footprint (as shown in FIGS. 11, 12A-12B, and 13) is elongated along the beam direction due to the low incidence angle 34. A low incident angle 34 is typical, for example, in Reflection High Energy Electron Diffraction arrangements, which, among other techniques can be used in the present system.

As the spatial resolution is not important for the uniformity of the film deposited on the substrate, an enlarged footprint formed where the electron beam is incident on the substrate (on the film) at a glancing angle is not an obstacle for the film composition analysis.

An impact of electrons on the material of the substrate (or the film) causes X-ray emission from the surface of substrate 18, and/or the film 20.

The X-ray emission is collected by at least one X-ray sensor assembly 36 located below the substrate (or the film) plane XY. The X-ray emission in the present system 10 is not limited to a specific azimuthal direction around z-axis. However, it has been found that the location of the sensor axis in a plane perpendicular to the long axis of the beam footprint ellipse provides optimal X-ray collection.

In an exemplary embodiment, the X-ray sensor 36 is positioned in the plane perpendicular to the long axis of the beam footprint ellipse, and at the angle (take-off angle) 38 of approximately 10 degree relative to the substrate (film)'s XY surface plane. The take-off angle 38 is the angle between X-rays counted by the X-ray sensor 36 and the substrate (or film) surface.

Figure 2A:
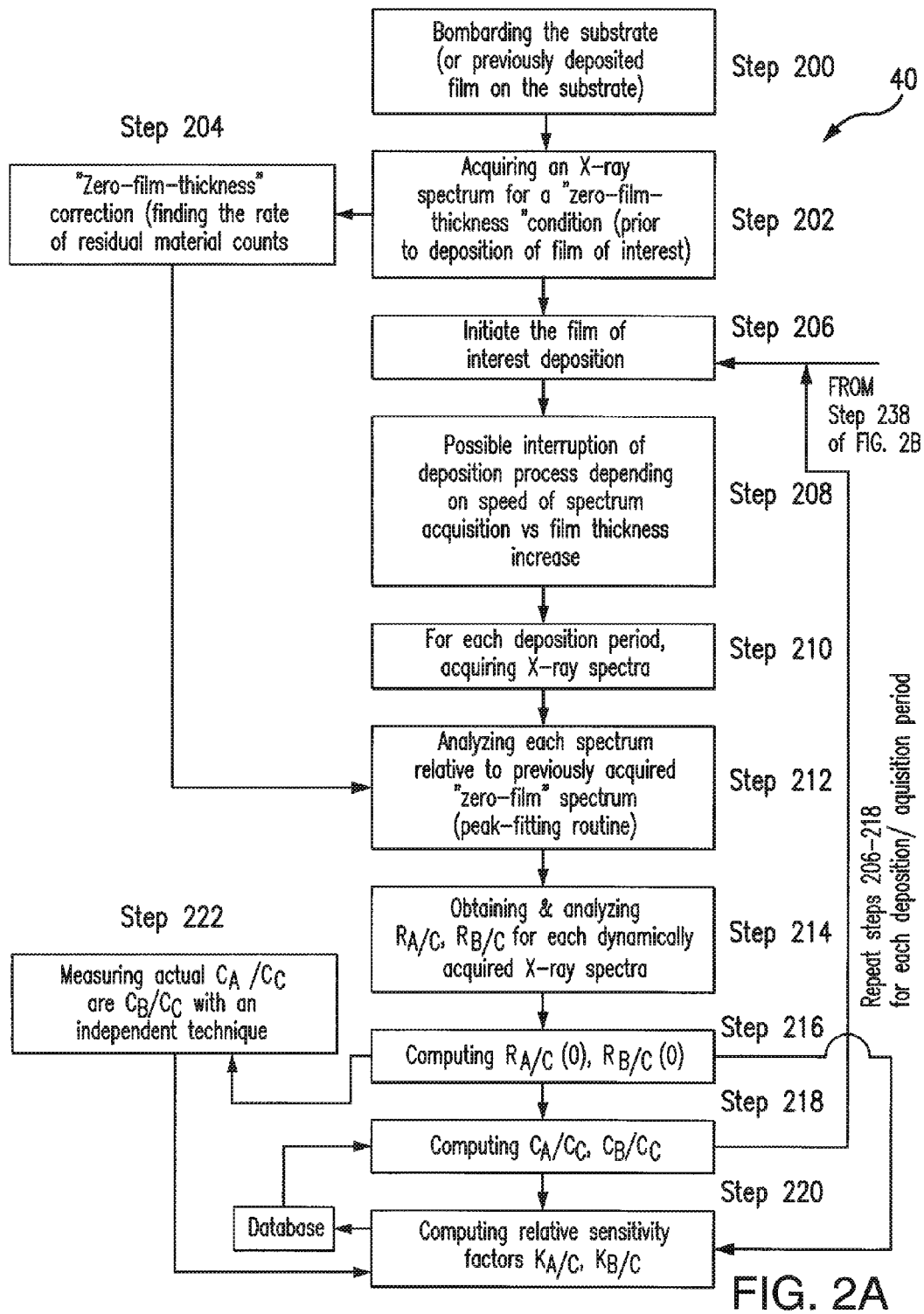
FIGS. 2A-2B are schematic representations of a step-by-step processing of the acquired spectra.
Figure 2B:
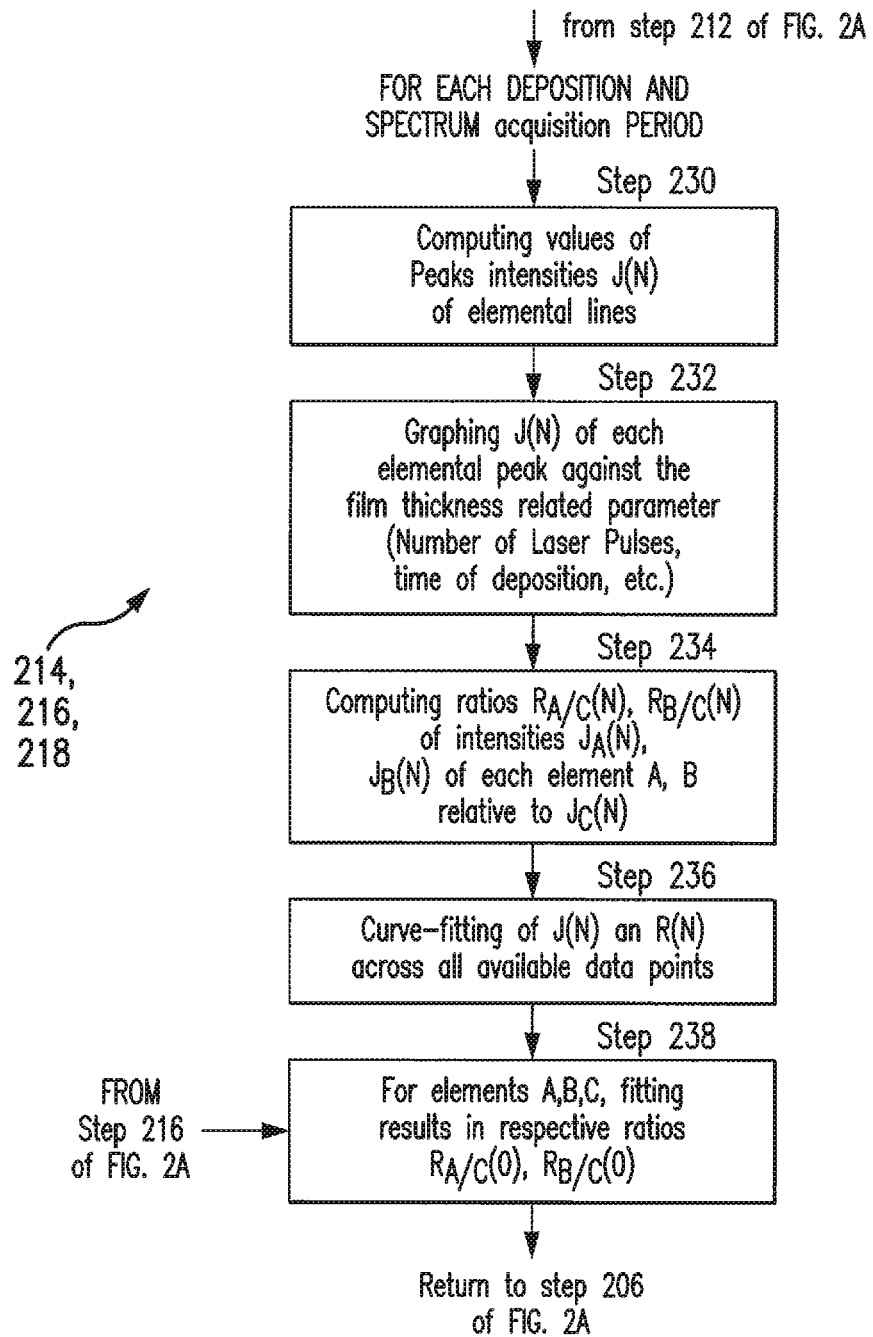

Referring to FIGS. 1 and 2A-2B, a control unit 40 is configured in the subject system to control its entire operation for the purposes intended, including control of the laser pulsing for the PLD, regimes of the electron beam generation and interaction with the substrate or film's surface, X-rays detection routine and regime of the X-ray sensor operation, as well as electronic beam X-ray data acquisition and processing, and execution of the algorithm for the subject compositional analysis routine.

The control unit 40 may be operatively coupled to (or operationally includes) a spectra acquisition unit 42 coupled to the X-ray sensor 36 to receive data corresponding to the generated X-ray emissions from the substrate and/or films deposited on the substrate 18 when exposed to the electron beam 32, spectra processing unit 44 operatively coupled to the spectra acquisition unit 42 to process the spectra acquired by the spectra acquisition unit 42, and a composition computation unit 46 operatively coupled to the spectra processing unit 44 to execute the computation of intensities of X-ray lines of the spectra, and composition of a film deposited on the substrate, and/or the composition of superposed films deposited on previously deposited films, as will be detailed in further paragraphs.

The proportionality factor between an elemental line intensity and the elemental concentration ideally would be a constant defined only by atomic parameters of the elements present in the film's material, and linearly related to the film thickness. In reality, however, the proportionality factor is not a constant as each element intensity measured by an external X-ray sensor is not only parametric (i.e., depends on concentration in a non-linear way), but also depends on the concentration and nature of other atoms present in the composition. Thus, the quantification of elemental concentrations is a complex endeavor.

Two phenomena contribute into the variability of the proportionality factor value:

(a) the fact that the spatial distribution of X-ray generation inside solid materials is parametric and not uniform; and (b) the X-ray intensity counted by an X-ray sensor is altered by the absorption of generated X-rays along their path to the film surface.

For thin films, the film thickness is an additional variable which strongly affects the spectrum of emitted X-rays. Even for a film of a known thickness, finding the chemical composition is a difficult task.

If a film under study is thin enough, the influence of these two phenomena can be minimized. If the thickness of the film is much smaller than the X-ray generation distribution depth, the X-ray generation within the film can be considered uniform. If the optical thickness of the film is much smaller than the characteristic X-ray line absorption length, the absorption effect may also be neglected. Thus, the ratio of X-ray intensities of elemental peaks for "very thin films" converges to a true constant for the elements' pair, and for a given measurements setup configuration, the ratio of the peaks intensities depends only on the ratio of elements concentrations, which is composition of the elements in the film. In practice, however, intensities available from very thin films are small, which results in an increased uncertainty in the measured value of the X-rays intensities ratio.

Moreover, when evaluating the composition of pre-deposited films of a significant thickness, only the ratio number at that particular thickness is available.

The subject method allows unique quantity of the ratio of elemental peaks intensities, also referred to herein as R(0), for a virtual film of zero thickness, and relates the R(0) directly to the film composition through a constant (for a given elemental pair A, B) relative sensitivity factor $K_{A/B}$ which is independent of the elemental concentrations and the film thickness.

An algorithm for obtaining a unique number, ratio $R_{A/B}(0)$ of intensities at zero film thickness of pairs AB of elemental X-ray lines of film containing elements A and B in an unknown proportion, operates through acquisition of preferably multiple spectra (but at least one spectra as the film thickness increases), which results in ratio data points graphed as function of a parameter proportional to corresponding film thickness, and the best fitting (preferably with a physically meaningful function) is executed across all the collected data points down to the virtual film zero thickness.

The procedure to obtain the composition of the film, i.e., the ratio of concentrations $C_A/C_B$ for each pair of the film's elements, as a product of $R_{A/B}(0)$ ratio number and a numerical factor $K_{A/B}$ that is independent of the elements concentrations, or film thickness, is constant for a given instrumental setup and is specific for the elements AB pair.

The subject method obtains the R(0) value by executing fittings with functions represented in Eq. 3 (for two J(N)), and function represented by Eq. 4 (for R(N)) of corresponding available data points for each elemental pair of interest.

Figure 7:
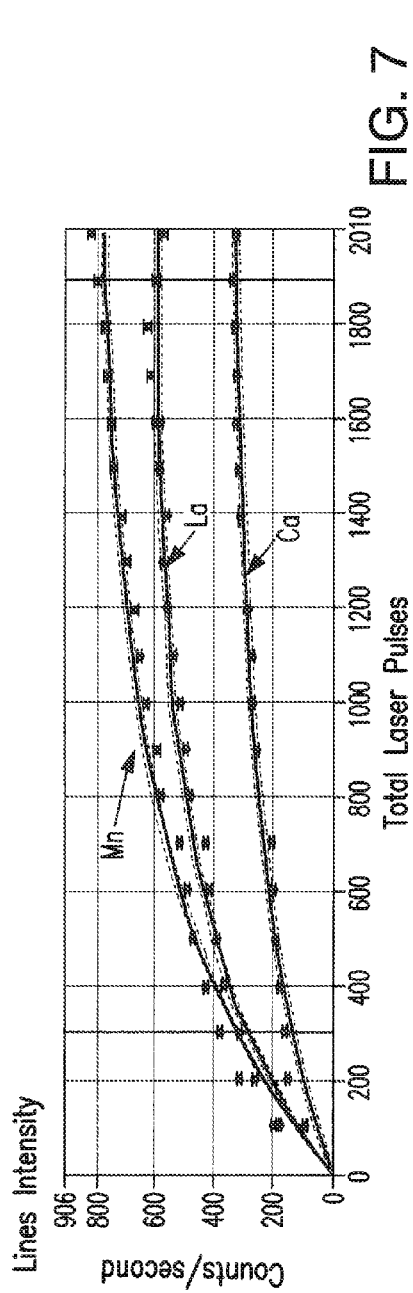
FIG. 7 is a diagram representative of X-ray elemental lines intensities J(N) as a function of a number N of the laser deposition pulses.
Figure 8:
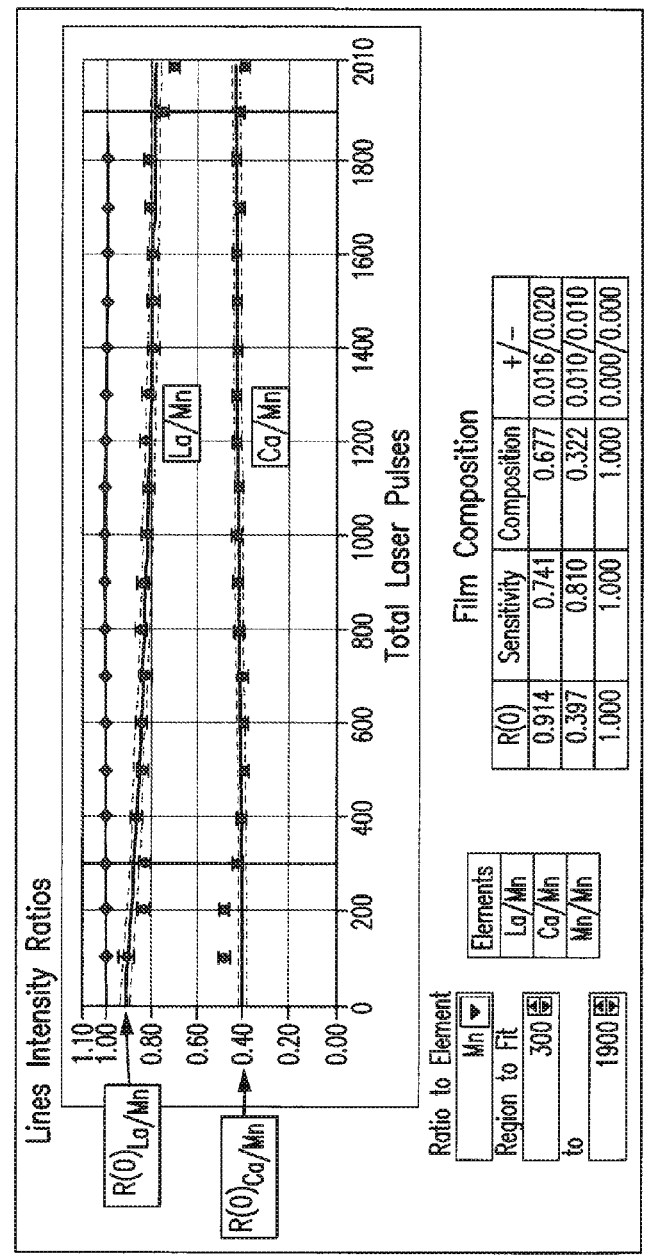
FIG. 8 is a diagram representative of ratios R(N) of the intensities J(N) as a function of a number N of the laser deposition pulses.

Intensities of elemental peaks quantified by the software serve as the basic data points used in executing the special algorithm of the subject method. Values of the obtained intensities J(N) of elemental lines are graphed against a corresponding number N of laser pulses, which represents the film thickness (as shown in FIG. 7). Ratios R(N) of the intensities J(N) to one of them are calculated and graphed, also as function of number N of deposition pulses, after each acquisition and processing, as shown in FIG. 8. Graphs of J(N) and of R(N) are displayed on the user interface 37.

Specialized software executes a curve-fitting of J(N) and of R(N) to provide a best fit across all available data points. As a preferred example, expressions presented by Eqs. 3-4 are used (wherein the variable H is substituted with N) to fit J(N), and R(N) dependencies.

FIGS. 2A-2B are representative of the subject in-situ routine which includes collecting multiple X-ray spectra from a film as its deposition thickness increases. The subsequent processing of the X-ray spectra underlies the subject method, which is further referenced to herein also as dynamic spectrometry method. The dynamic spectrometry method analyzes the changes in X-ray spectrum, applies a unique algorithm to process the spectra, and obtains R(0)-numbers whose value is linked directly to the ratio of concentrations $C_A/C_B$ of the film elements A, B, i.e., to the composition.

In a measurement setup, a constant factor $K_{A/B}$ for A, B elemental pair links the measured $R_{A/B}(0)$ value and the film composition. Since the factor $K_{A/B}$ is a constant, its value can be found by running the method routine when depositing the film of any A/B concentrations proportion, and determining the deposited film composition by an independent technique. The determined value $K_{A/B}$ is subsequently applied to find the unknown $C_A/C_B$ composition in any other film deposited in the setup. With other system parameters fixed (sensor parameters, collimation, electron energy, beam incidence and X-ray take-off angles, etc.), the $K_{A/B}$ factors of elemental pairs are the system constants which may be referred to as relative sensitivity factors.

Physical foundation for the subject method can be illustrated by the simplified mathematical model detailed in further paragraphs.

A profile of the X-ray density generated by electrons at depth Z inside a film can be described as an exponent $$\sim \exp(-Z/Le) \quad \text{(Eq. 1)}$$

with the characteristic length Le.

The intensity of X-rays emitted from the film surface and counted by an X-ray sensor is less than the intensity of X-rays generated within the film volume. The emitted intensity is reduced due to the absorption of the X-rays along its optical path in the film. This reduction can be also described as exponential $$\sim \exp\{-[Z/\sin(\Phi)]/Lx\}, \quad \text{(Eq. 2)}$$

where Lx is the characteristic length of an X-ray line absorption, $Z/\sin(\Phi)$ is the optical path of the X-ray, and $\Phi$ is the incidence angle of the electron beam to the film surface.

Both exponents (Eqs. 1-2) can be combined with an effective spatial scale L defined by the relation $$1/L = 1/Le + 1/(Lx \sin(\Phi)) \quad \text{(Eq. 3)}$$

The Le and Lx are not constant, but are parametric, i.e., they depend on element concentrations.

A density of the generated atomic X-rays is proportional to the concentration C of atoms in the material under study. Total intensity J(H), per a unit of the electron beam current density, received by the X-ray sensor from a film of thickness H is found by integrating the exponential distribution from the substrate surface at Z=0 to the film thickness Z=H.

$$J(H) = F\,C\,L[1 - \exp(-H/L)] \quad \text{(Eq. 4)}$$

where F is a constant for a given chemical element factor which characterizes electron-atom interaction required for the X-ray line quantum generation, and also characterizes the specifics of the X-ray sensor for the X-line in question.

A Ratio $R_{A/B}$ of such intensities $J_A(H)$ and $J_B(H)$ for elements A and B is $$R_{A/B}(H, L_A, L_B) \equiv J_A(H)/J_B(H) = [(F_A/F_B)(C_A/C_B)(L_A/L_B)]$$
$$[1 - \exp(-H/L_A)]/[1 - \exp(-H/L_B)] \quad \text{(Eq.5)}$$

The composition $C_A/C_B$ cannot be obtained directly from the measured ratio $R_{A/B}(H)$ value due to its thickness dependency (and the thickness H itself might be unknown), and to the fact that $L_A$, $L_B$ parametric factors are both composition dependent, even if the atomic and instrumental factors F are known.

In the subject dynamic spectroscopy method, however, an advantage is taken of analyzing multiple experimental spectra, including the spectrum acquired from the substrate without the film, and also as the film's thickness H is gradually increased by deposition (through acquisition and processing of the X-ray spectra at a number of stages, also referred to herein as steps, of the deposition process, until the deposition process has been completed).

By obtaining and analyzing $R_{A/B}(H)$ dependence, the method provides determination of the number $R_{A/B}(0)$.

Despite the fact that each X-ray line intensity J(H) approaches zero as the thickness approaches zero, the ratio of intensities at zero thickness is a finite number $R_{A/B}(0)$. The number $R_{A/B}(0)$ has a unique property. It follows from Eq. 5, zero-thickness ratio $R_{A/B}(0)$ is independent of the characteristic lengths $L_A$, $L_B$, and is directly related to the material composition via the atomic and instrumental factor $F_A/F_B$ which is a constant for a given instrumental setup.

$$R_{A/B}(0)=(F_A/F_B)(C_A/C_B) \quad (Eq.6)$$

Thus, the film composition $C_A/C_B$ follows immediately from the determined $R_{A/B}(0)$ value as $$C_A/C_B=(F_B/F_A) \cdot R_{A/B}(0) \equiv K_{A/B} R_{A/B}(0) \quad (Eq.7)$$

Here $K_{A/B}$ is a relative sensitivity factor for the elemental pair A, B.

The relation in (Eq. 7) (despite the similarity to the known Cliff-Lorimer expression $C_A/C_B = K_{A/B} \cdot J_A/J_B$ with the factor $K_{A/B} \equiv F_B/F_A$), differs from the Cliff-Lorimer expression in an important aspect, i.e., the factor $K_{A/B}$ in Eq. 7 is constant for the elemental pair A, B, and at the zero film thickness it does not require application of any ZAF-corrections techniques to account for the thickness-related effects.

As the measured $R_{A/B}(0)$ number is also thickness independent, the subject method provides a straightforward way of determining the composition with a minimal involvement of physical constants and complex calculations, i.e., once collective effects (such as X-ray absorption and fluorescence) are eliminated from the analysis for infinitely small thickness, only atomic, instrumental, and concentration factors remain to control X-ray intensities.

Although various functions can be used to provide the best fit for the $R_{A/B}(H)$ dependence and obtain $R_{A/B}(0)$ value from the fitting, in the subject method, the function described in Eq. 5 can be used for fitting.

An important feature of the subject method is that, in order to find $R_{A/B}(0)$, it is not necessary to know the actual values of the film thicknesses at which the spectra are taken. It is sufficient to know only a value directly related to the thickness. In an exemplary case of the pulsed laser deposition, wherein the thickness is proportional to the number of deposition laser pulses applied, the number of pulses N can be used instead of the film thickness H to obtain the R(N) dependence.

Figure 3:
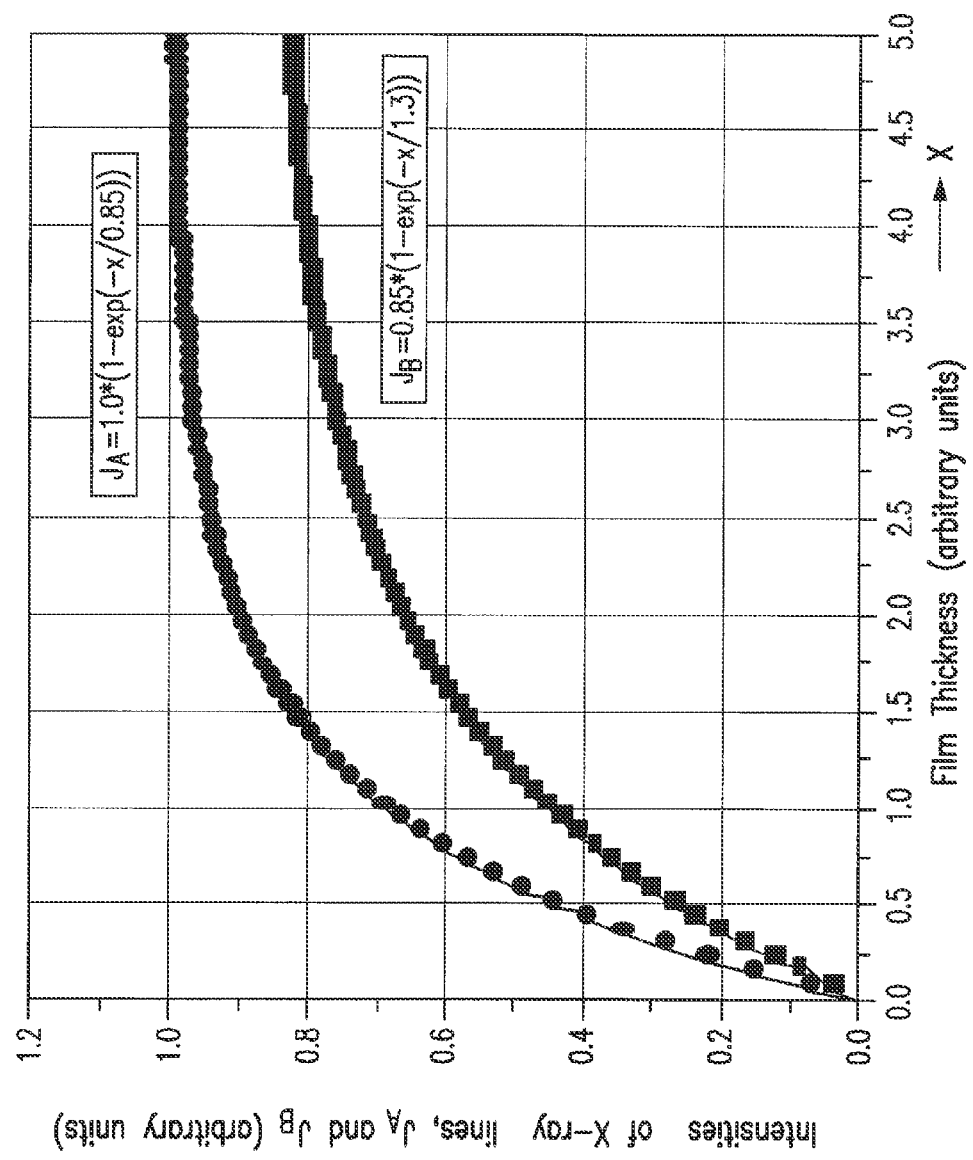
FIG. 3 is a diagram representative of functional dependence of Intensities $J_A$ and $J_B$ of X-ray lines A and B on a film thickness X.
Figure 4:
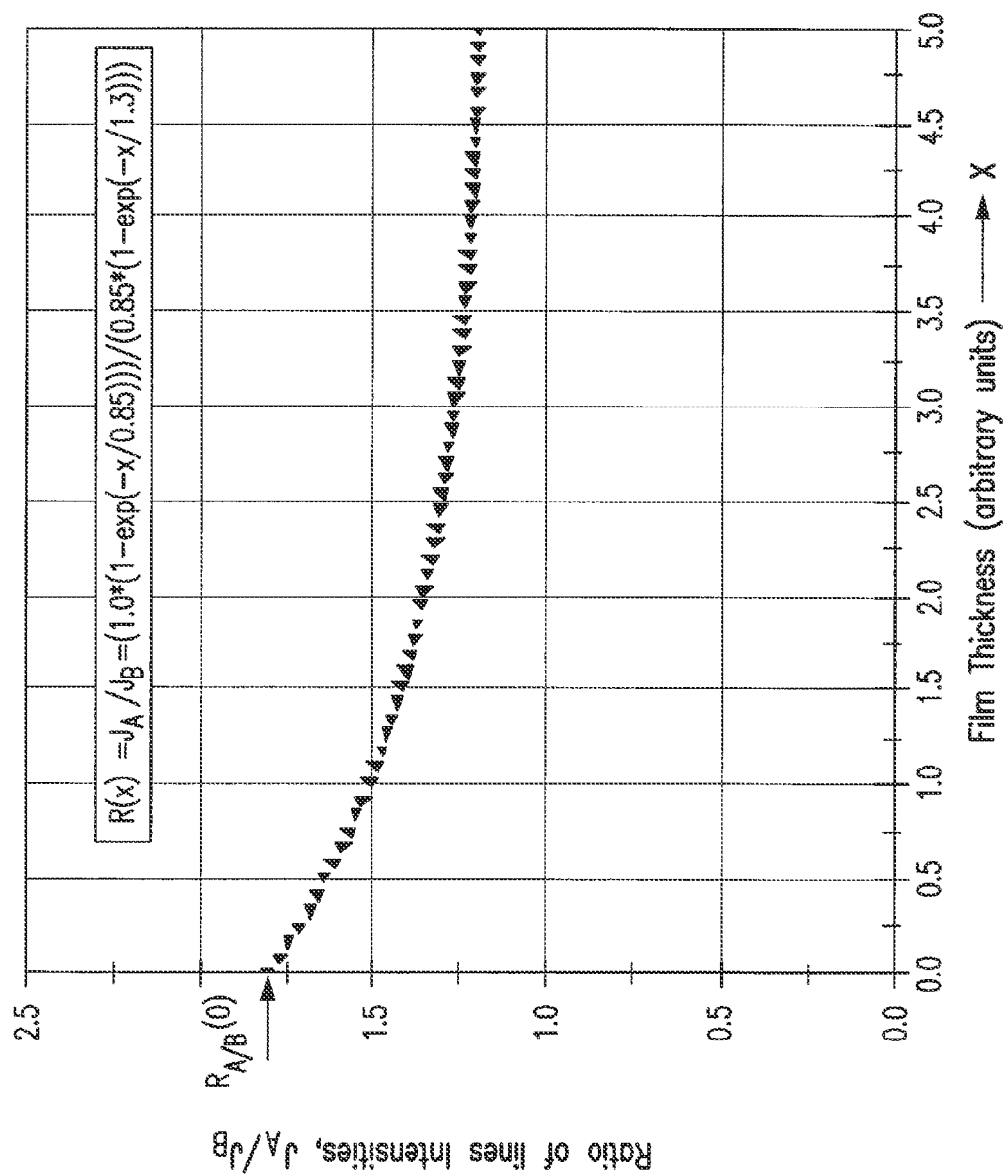
FIG. 4 is a diagram representative of a dependence of the Ratio R of the Intensities $J_A/J_B$ vs. the film thickness X.

In another exemplary case of the continuous rate deposition, total deposition time T after which each spectrum is acquired can serve as the thickness measure, and thus R(T) dependence may be used instead of R(H). FIGS. 3-4 illustrate the behavior of the J(H) and R(H) functions, respectively.

In one of the examples of the subject method, the Pulsed Laser Deposition technique was used for creating the films. In this technique, application of each laser pulse increases the thickness of the film by a specific amount, and the total number of applied laser pulses can serve as a measure (units) of film thickness.

As an example of the technique for acquiring the X-ray spectrum, the Energy Dispersive Spectrometry (EDS) may be used, and for example, the DTSA-II, multiplatform software package can be used for quantification of X-lines peaks intensities.

X-ray spectrum represents a distribution of X-ray intensities among X-quanta channels. Each chemical element manifests itself by a peak located at a certain energy (keV) location, which is known as the characteristic energy of the chemical element.

The acquired X-ray spectrum is subsequently processed with a peak-fitting software program. In the present embodiment, as an example, the XRS-FP, X-ray spectrum analysis software by AMPTEK is used for spectra processing. The processing results in values of intensities of the X-lines peaks expressed, for example, in units of counts per second.

At least one X-ray sensor is employed to acquire radiation from at least a part of the beam footprint on the film surface, which is the source of the X-rays. A total field of view of the X-ray sensor can be intentionally limited however in order to reduce the amount of undesirable X-rays received.

Referring to FIGS. 2A-2B and 1, execution of the subject method begins in step 200, where the Control Unit 40 initiates generation of the electronic bream and bombarding of the substrate 18 (or previously deposited film-on-the substrate), also referred to herein as an underlying structure.

Prior to executing the subject method, electron beam current is stabilized, and the e-beam is aligned, at least partially, with an area of interest at the film surface (beam footprint). As an example, the Electron beam source manufactured by Staib Instruments can be used.

The logic 40 further flows to step 202, where the spectra acquisition sub-system 42 acquires the X-ray spectrum prior to a film of interest being deposited on a substrate (or atop a previously deposited layer). Such "zero-thickness" spectrum represents mostly elements of the substrate material or the substrate covered by a previously deposited film (referred to herein as a previous film).

If the superposed (new) film of interest contains elements different from the elements of the previously deposited film, new X-ray elemental peaks appear at different energy location of the spectrum, and can be distinguished from the X-ray spectra peaks of the previous film.

At the step 202 of the subject method, even if the superposed new film of interest has not yet been deposited, the spectrum of such "zero-thickness" film might contain some counts at the locations of X-ray lines corresponding to the elements of the new films. Such spurious counts may originate from the substrate mounts, vacuum chamber walls, etc., the surfaces of which might contain residual material of previous depositions in the system. Signals of such unwanted sources can contribute and distort values of intensities measured for the new film 20, especially when it is thin. Ratios of such peaks intensities can also be different from the ratios of elemental peaks intensities in the new film 20 of interest, thus distorting the results of the analysis.

The logic 40 further flows to step 204, to execute the "zero-film" correction routine designed to minimize the effect of contribution of unwanted materials in the results of the analysis. The subject method uses the "zero-film" correction spectrum data in order to make corrections for the spurious counts for all following spectra acquired from the new deposited films. This correction operation has proven to be useful, especially in the beginning of the film growth, when X-ray intensity produced by new films may be relatively small.

Figure 5:
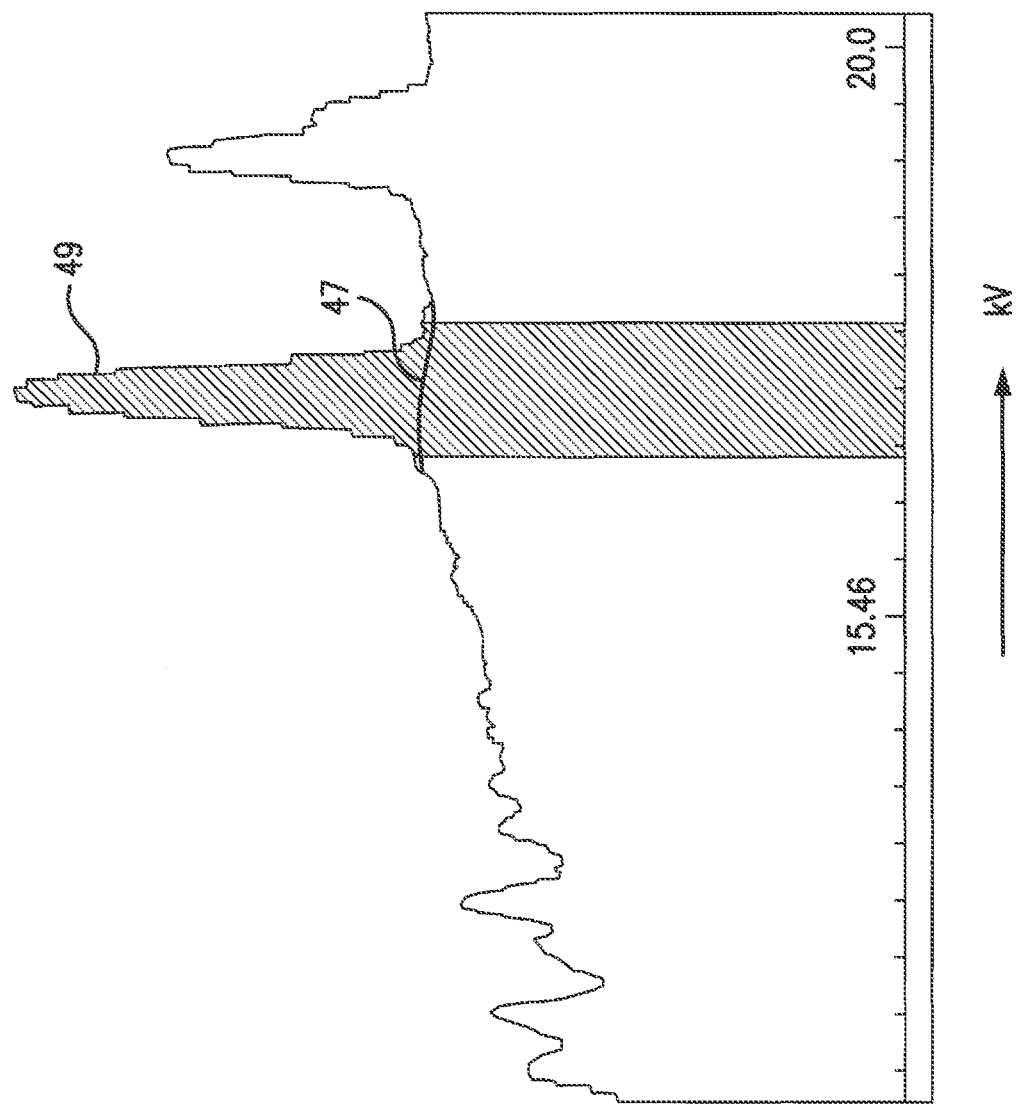
FIG. 5 is representative of the X-ray spectrum collected before the film deposition, i.e., "zero film-thickness" spectrum.

The "zero-film" correction is a mathematical operation executed on raw data of the acquired spectra in order to remove contributions of the remnant material intensities, and arrive at true intensities produced exclusively by the newly deposited film. As shown in FIG. 5, in the correction procedure, line 47 connects intensities of the peak of interest 49 at its left and right sides. The intensity counts of the peak 49 above the line 47 originate from the residual material, and the counts below the line originate from the spectrum continuum, which is present, even if there are no residuals.

In the correction routine, the residual counts (i.e., above the line 47) acquired in each channel of the spectrometer are divided by the net time of the spectrum acquisition, in order to find the rate of the residual material counts accumulation in each channel of the peak. Each following raw spectrum acquired from the deposited film is then corrected by subtracting the counts produced by the residuals (in step 212).

In each channel, a number of subtracted counts is proportional to the corresponding residuals accumulation rate and the acquisition time. Similar corrections can be executed at several peaks of interest.

In the following step 206, deposition of the film 20 of interest is initiated by the control unit 40 commanding the laser generating laser beam 22 bombarding the material target 26 and evaporating the material 14 to be delivered onto the surface of the substrate 18 (or a previously deposited film) to grow the film 20 of interest, as shown in FIG. 1.

In step 208, the deposition may be interrupted in order to prevent an excessive change of the thickness during the spectra acquisition. However, if the spectrum acquisition is faster than the film thickness increase, no interruptions are necessary.

In the following step 210, a portion 16 of a deposition material 14 is deposited (on the substrate 18 or on the previously deposited film) by applying a specific number of laser pulses, and the X-ray spectrum from the formed film is acquired.

In step 212, the acquired spectrum is subsequently processed in the Spectra Processing sub-system 42 through a peak-fitting routine in order to identify elemental peaks by their energy position, remove continuum background, extract peaks counts, fit and integrate them, etc., and arrive at values of peaks intensities, expressed, for example, as counts per second. For example, the XRS-FP software (Amptek, Inc.) can be used.

Figure 6:
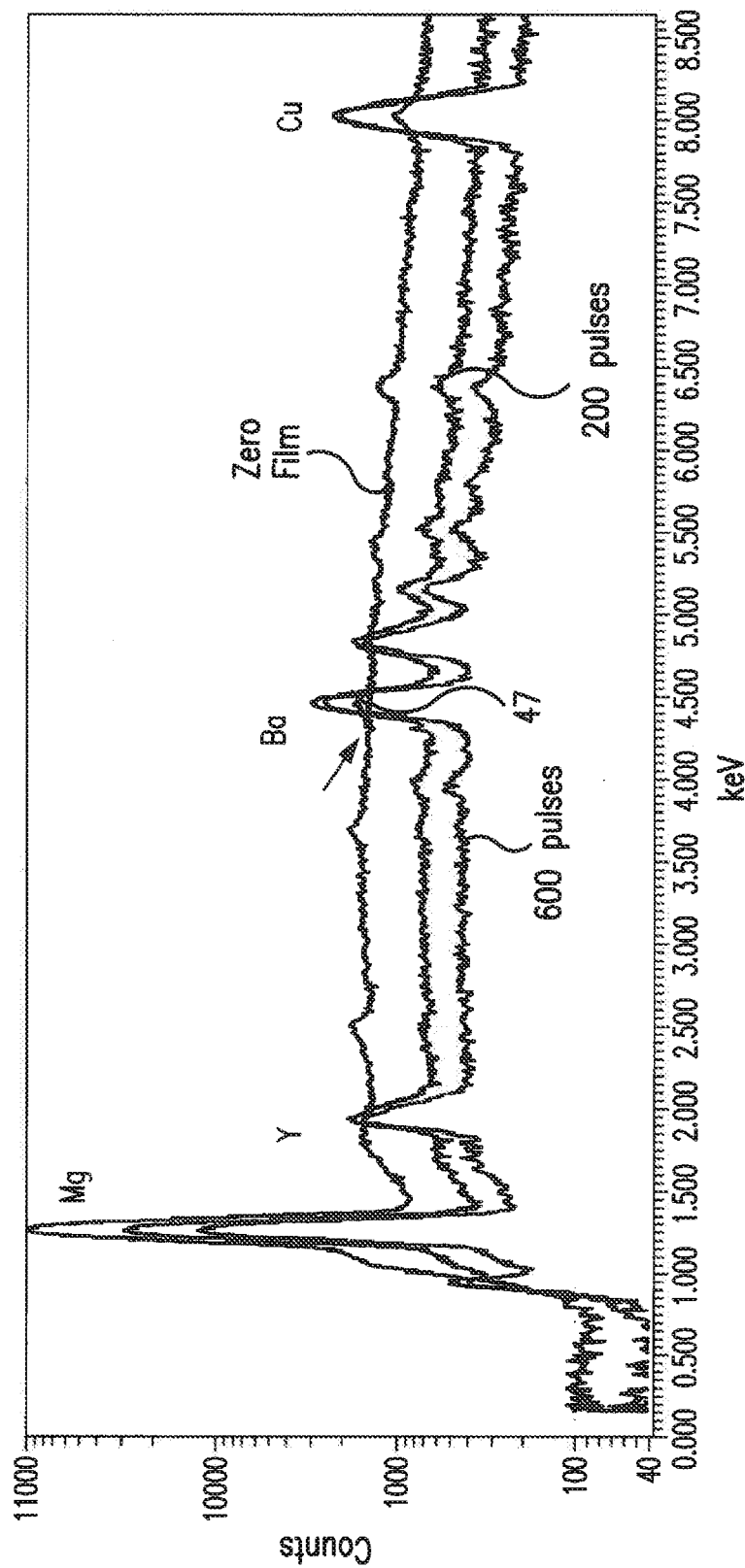
FIG. 6 is a diagram representative of the spectra acquired from films deposited with different number of laser pulses, including zero pulses.

FIG. 6 shows an example of the spectra acquired from the bare substrate ("zero-film" spectrum), from film deposited with 200 pulses, and 600 pulses. For MgO used as the substrate material, the spectra contains a strong X-ray peak of Mg.

In the diagram presented in FIG. 6, the film composition includes Y, Ba, and Cu. The intensities of the peaks corresponding to Y, Ba, and Cu, respectively, increase with the number of applied laser pulses. An arrow in FIG. 6 points to the line 47 on the "zero-film" spectrum which is used to apply the "zero-film" corrections in step 212 as described in previous paragraphs.

The intensities of the elemental peaks (Y, Ba, Cu) quantified by the peak-fitting software, serve as the basic data points used in executing the special algorithm of the subject method. Values of the obtained intensities J(N) of the elemental lines, shown in FIG. 7, are graphed against the corresponding number N of laser pulses, which, in this exemplary implementation, represents the thickness of the film 20. Returning to FIGS. 2A-2B and 1, in the subsequent step 214 of the Spectra Processing sub-system 44 of the routine 40, the Ratios R(N) of the intensities J(N) of each element (La, Ca) relative to one of them (Mn) are calculated and graphed as a function of the number N of deposition pulses (as shown in FIG. 8) after each acquisition and processing. Graphs of the J(N) and of the R(N) are displayed on a user interface 37.

Subsequent to step 214, the $R_{A/C}(0)$ and $R_{B/C}(0)$ are computed in step 216, as will be detailed in further paragraphs.

The routines (deposition-acquisition-processing-fitting) are repeated until the number of data points that is sufficient for determining the composition with a desired uncertainty is obtained. Typically, the greater number of spectra is acquired, the better is the certainty of the composition determination. Value(s) of R(0) can be determined simultaneously for every film elemental pair of interest.

It has been found experimentally that the more data points are used for the fitting, the better is the accuracy of R(0) determination. However, even a single non-zero thickness data point R(N) provides some estimate of the R(0) value.

In step 218 (FIG. 2A), an actual film composition $C_A/C_C$, $C_B/C_C$, for each elemental pair in the film under study is calculated from the measured $R_{A/B}(0)$ values by applying a relative sensitivity factor $K_{A/B}$ which is computed in step 220 in accordance with Eq. 7, i.e., $(C_A/C_B=K_{A/B} \cdot R_{A/B}(0))$. The composition computed in step 218 is constantly updated after each new period of deposition/acquisition process.

In the example, represented in FIG. 8, the relative sensitivity factors $K_{La/Mn}=0.741$ and $K_{Ca/Mn}=0.81$ are used which are pre-determined for the system. Subsequently, the composition of the film relative to Mn is determined as La/Mn=0.741×0.914=0.6.77, and Ca/Mn=0.397×0.810=0.322. Thus the film composition (in chemical format) is $La_{0.677} Ca_{0.322} Mn_1$, as output on the interface 37.

The procedure of determining the relative sensitivity factors $K_{A/C}$, $K_{B/C}$ in step 220 includes the following steps:

(a) executing the routine of the subject method while depositing a calibration film that contains A, B, C-elements in any proportion, and measure the $R_{A/C}(0)$, $R_{B/C}(0)$ values of the film;

(b) determining (in step 222) the composition $C_A/C_C$ and $C_B/C_C$ of the calibration film ex-situ (with an independent technique, for example, Rutherford backscattering, mass-spectrometry, etc.); and (c) subsequent to determination of the values $R_{A/C}(0)$, $R_{B/C}(0)$ and $C_A/C_C$, $C_B/C_C$ for the calibration film, the data from steps 216 and 222 are fitted into step 220, and the relative sensitivity factor of the elemental pair is computed as $K_{A/C}=(C_A/C_C)/R_{A/C}(0)$. Correspondingly, $K_{B/C}$ is computed as $K_{B/C}=(C_B/C_C)/R_{B/C}(0)$.

The sensitivity factor K (determined once for the system setup) is a constant which can be applied to determine composition of, for example, AB elements in other films deposited within the system. The sensitivity factors $K_{A/B}$ for many elemental pairs can be determined and saved in a library (database). These factors have the following properties: $K_{A/B}=1/K_{B/A}$, and $K_{A/B}=K_{A/C}/K_{B/C}$. Thus, there is no need for an additional system run to determine $K_{A/B}$ once $K_{A/C}$ and $K_{B/C}$ are determined.

FIG. 2B details the execution of the subject logic in steps 214, 216, 218. As shown in FIG. 2B, for each spectrum acquisition (in a respective stage of the deposition technique), values of peaks intensities J(N) of elemental lines are computed in step 230.

In the following step 232, intensities $J_A(N)$, $J_B(N)$, $J_C(N)$ of each elemental peak for the elements A, B, C, are graphed against a parameter which serves as a measure of the film thickness, for example a number N of laser deposition pulses, as shown in FIG. 7.

The logic further flows to step 234, where ratios $R_{A/C}(N)$, $R_{B/C}(N)$ of intensities $J_A(N)$, $J_B(N)$, of each elemental peak (for elements A, B) relative to the element, for example C, intensity $J_C(N)$ are graphed against the N, as shown in FIG. 8.

In the subsequent step 236, the logic applies a curve-fitting function for J(N) and R(N) across all available data points to provide a best fit across all available data points. As an example, the expressions (Eq. 4 and Eq. 5) wherein the variable H is substituted with N may be used to fit J(N) and R(N) dependencies, accordingly, and in step 238, results computed in step 236, are fitted in respective $R_{A/C}(0)$, $R_{B/C}(0)$ for each pair of elements A/C, B/C as shown in FIG. 8.

For every elemental pair A-B, in step 238, results are fitted in an unique number (i.e., the value $R_{A/B}(0)$ of the ratio at the "zero film" thickness), which relates directly to a relative content of the elements in the film (i.e., the composition). As the film composition is a relative number, ratio numbers relate directly to film composition. The $R_{A/B}(0)$ is shown in FIGS. 4 and 8. After step 238, the logic loops to step 206 as shown in FIG. 2A.

The subsequent data points are obtained by repeating the procedure presented in FIG. 2B and steps 206-218 of FIG. 2A, through the steps sequence, including: deposition-acquisition-processing-fitting in each deposition stage, and the composition $C_A/C_C$ and $C_B/C_C$ is updated after each deposition/acquisition period. After completing each routine, new points are added to the J(N) and R(N) graphs, their fittings are updated, and an updated value R(0) is determined.

The subject method is not limited to determination of the chemical composition in a single film 20 on the substrate 18, but is capable of determining compositions of multiple films deposited atop the films deposited earlier. As soon as the new (superposed) film 20 contains elements different from the elements of the underlying (old) film, the combined structure "old film on the original substrate" can be treated as another substrate (different than the original substrate), and the subject method, routine and analyses algorithm may be applied to obtain the composition of the new (superposed) film. Peaks of the new film appear at locations of X-ray spectra different than the peaks of the underlying combined "old film on the original substrate" structure (referred to herein also as a underlying structure), thus enabling execution of the subject routine.

The method also has capability to determine the film thickness. The film thickness determination can be performed in-situ, and real-time updated while the film deposition is progressing. Such capability is based on the analysis of the intensity Js of the X-ray peak of the substrate Js.

The intensity Js(0) is at its maximum initially, when no film covers the substrate. As the film thickness increases with the number of the laser pulses N, the intensity Js(N) decreases due to the lower fraction of incident electrons capable of penetrating the film and to cause X-rays generation in the substrate. A larger absorption of the X-rays also occurs in the thicker film as it has been deposited.

A normalized intensity Js(N)/Js(0) of the substrate X-ray peak is equal to unity initially, and a degree of its decrease can serve as a measure of the film thickness.

In the subject method, the normalized intensity Js(N)/J(0) is calibrated once against the film thickness for a given pair "substrate element-film material". Then the calibration is applied for calculation of the film thickness in real-time.

Figure 9:
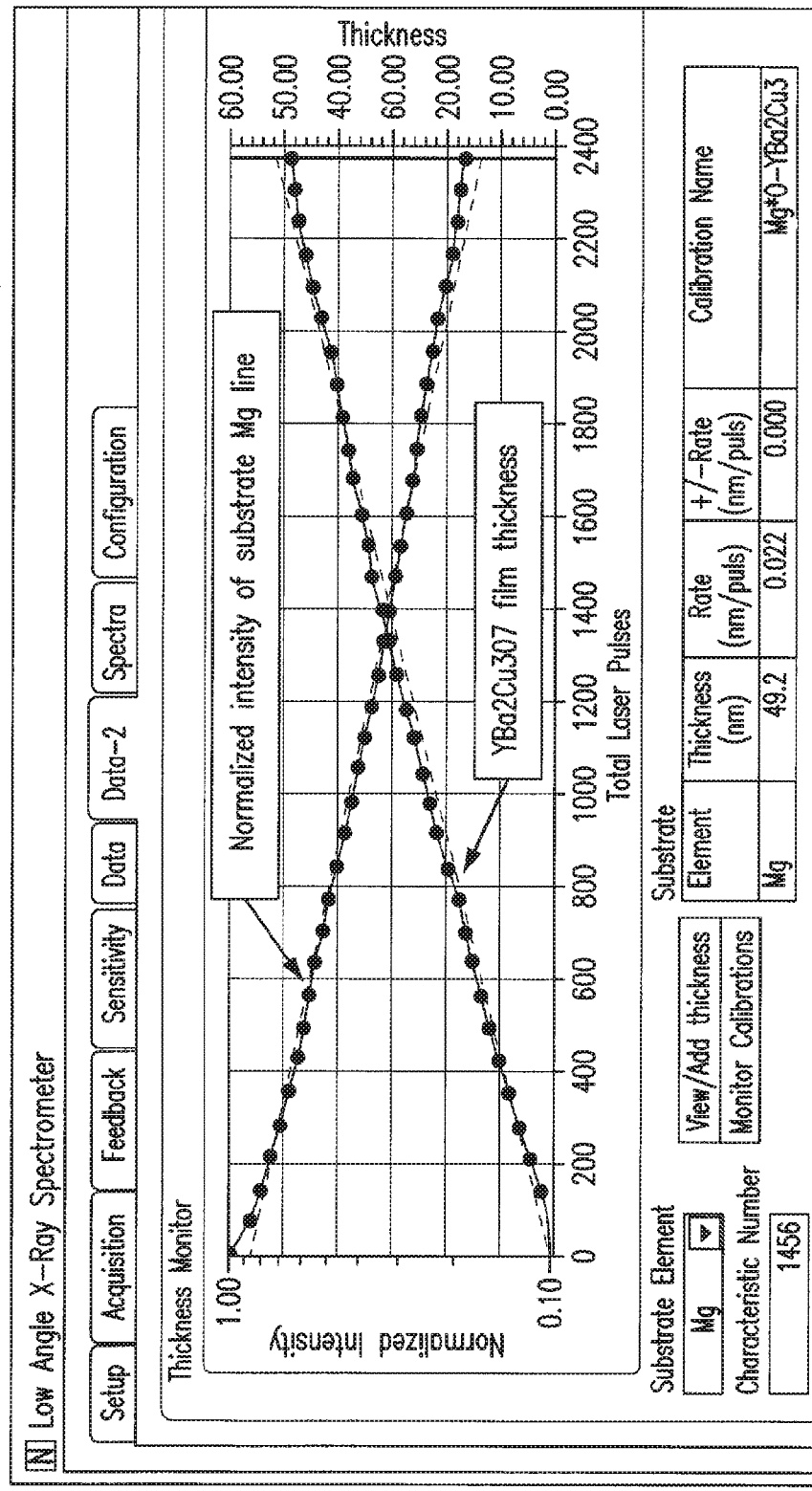
FIG. 9 is a diagram representative of a decrease in the normalized intensity of the X-ray lines of the substrate material as a function of the number of the film deposition laser pulses.

It has been found experimentally that a decrease in the normalized intensity can be described as an exponential decay with the increase of the film thickness (for example, number of laser pulses) accurately. An example of such decay is shown in FIG. 9. The decay is fitted with function $$Js(N)/Js(0)=A\cdot\exp[-N/Ns], \quad (Eq.\ 8)$$

where Ns is a characteristic number of laser pulses. The number of pulses Ns corresponds to a characteristic film thickness Hs characterizing such decay $$Js(N)/Js(0)=A\cdot\exp(-H/Hs) \quad (Eq.\ 9)$$

For the calibration of the decay relative to a thickness, a deposited film thickness is measured once, and Hs value constant is determined. Having the values of factors A and Hs determined, the current film thickness H(N) is calculated in accordance with Eq. 9 from the measured level of the normalized substrate intensity Js(N)/Js(0), i.e., Eq. 8. Updated values of the film thickness are displayed on the user interface.

As shown in FIG. 9, YBa2Cu3O7 is being deposited on the MgO substrate, and the normalized intensity of elemental line corresponding to Mg is used to measure the current film thickness and the deposition rate. Average film deposition rate (for example, in units nm/pulse) is calculated as H(N)/N.

In addition, the subject method has a capability to process several X-ray lines of the substrate simultaneously in order to optimize sensitivity and accuracy of the film thickness monitoring.

In the subject system 10, as presented in FIG. 1, the angle 34 at which the electron beam 32 is incident to the film 20 can be selected to maximize the efficiency of X-ray generation.

A general difficulty of the X-ray thin films spectroscopy with the electron beam excitation is that the excited volume of the film's material is greater than the film thickness. Thus, the normal (perpendicular to the surface) beam incidence angle used in typical electron probe microanalysis setups, causes an inefficient process of generation of X-rays from films. Typical range of 30 kV electrons in solid materials is ~2 microns which is larger than the thickness of the films of interest, and the probability is low for a normally incident electron beam to produce atom ionization and X-quanta as it travels across thin film.

Although not limiting the electron beam incidence angle to specific values, in the preferred implementation, the system 10 uses electron beams 32 with a small glancing (relative to the film surface) angle 34, i.e., angle α of the electron beam incident on the film (or substrate) in order to maximize the efficiency of X-ray generation in the film 20.

Figure 10:
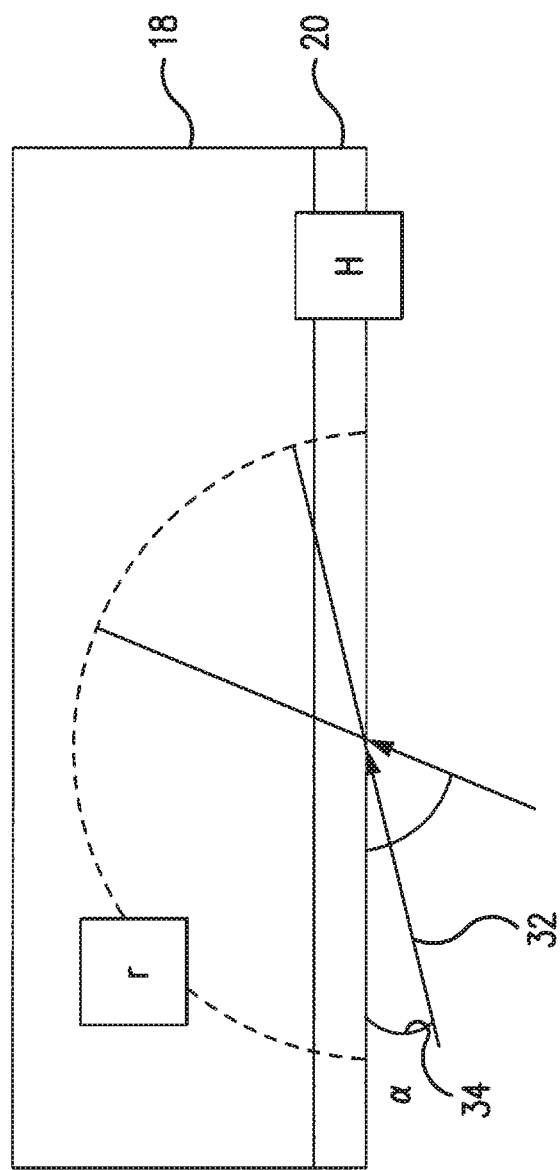
FIG. 10 illustrates an advantage of using a small electron incidence angle geometry in the subject system to increase X-ray generation in the film.

With the small angle geometry, as illustrated in FIG. 10, the length r of the electron trajectory within the film 20 is sufficiently larger than at normal α=90 degree incidence. With the total travel range r fixed by the electron energy, the small angle geometry increases the fraction of the energy which an electron spends on the X-rays generation in the film. For example, a path of an electron incident at the glancing angle 34 of 2.7 degree is ~20 times larger than the film thickness H.

Assuming the electron travel range along the beam 32 direction equals r, and assuming that the electron generates uniform number of X-rays per unit of the travel length, the amount of X-rays generated while the electron is traveling inside the film 20 (of thickness H), and inside the substrate 18, are proportional to corresponding lengths. The in-film path is H/sin(α), while the in-substrate path is r−H/sin(α). Thus, the fraction of X-rays generated in the film 20 relative to the total X-rays generated along its entire path is (H/r)/sin(α). At small angles (α<<1 degree), the electron energy is used more effectively for generation of the X-signals from the film 20.

With the incidence angle 34 of the electron beam less than 3 degree (a typical angle of electron elastic scattering), a large fraction of electrons is scattered out of the film, and thus cannot be used effectively to generate X-rays. Thus, the incidence angle 34 between 3 and 45 degree is recommended in the subject system. More preferable, the incidence angle 34 ranges between 3 and 15 degrees, and in the most preferable arrangement, between 3 and 6 degrees.

As presented in FIG. 1, another aspect of the subject system's design addresses a selection of the angle 38 relative to the substrate surface at which the sensor 36 collects X-rays emitted from the surface of the substrate 18 or the film 20. The angle 38 is commonly called the "take-off" angle. In the subject system, the take-off angle 38 is selected within a preferable range defined by both the physical X-ray propagation, and the specific geometry of the system 10 to optimize its performance.

The take-off angle 38 is set larger than the "angle of total external reflection" of X-rays. In contrast to the visible range optics, X-rays refractive index of materials is smaller than unity. Thus, X-rays traveling from the material volume experience total reflection from the surface if the incidence angle (of the X-rays to the surface) is smaller than a critical value. From the point of view of the X-ray sensor 36, located outside of the material, no X-rays can be detected at a take-off angle less than the critical angle. Thus in the system 10 supporting the subject method, a take-off angle value which is greater than the critical angle is to be used.

The critical angle value increases with the mass of an atom emitting X-ray, and decreases with the energy of the X-ray photon. Thus the worst scenario (largest critical angle) is expected for the heaviest atoms of interest, and for the smallest X-ray energy which the sensor can count.

For example, for Mg-Ka line (1.25 keV), and the critical angle of ~1.2 degree, the take-off angle is 3.1 degree for Cu—La line (0.928 keV), and 0.43 degree for Ni-Ka line (7.47 keV).

X-rays exiting the surface at an angle in vicinity of the critical angle tend to concentrate (have a maximum intensity) around the electron beam incidence angle. That makes the X-ray intensity highly sensitive to the exact take-off angle value, which makes it problematic to quantify the intensity of the spectra peaks for the purpose of the subject compositional analysis.

Based on the considerations presented in previous paragraphs, an optimal take-off angle in the subject system 10, is greater than critical angles, i.e., greater than 3 degrees, and preferably greater than 4 degrees. With such take-off angles, the angular dependence of X-ray emissivity is nearly leveled, which makes the method results more stable. The maximum value of the optimal take-off angles is limited at about 20 degree.

Figure 11:
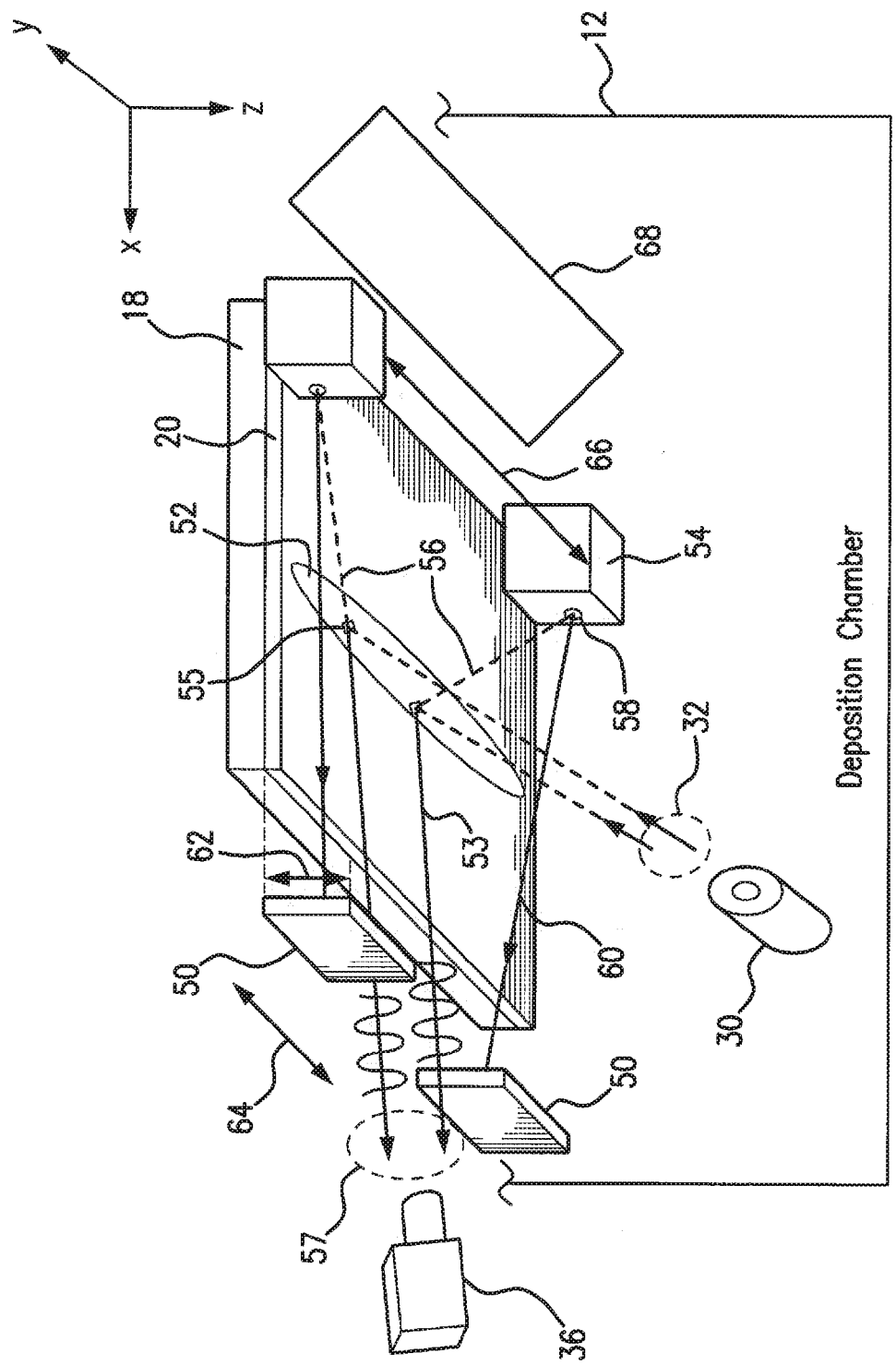
FIG. 11 is a schematic representation of the subject system detailing the arrangement employing the X-ray gate-shield for prevention of acquisition of undesirable X-rays which originate from objects foreign to a newly-deposited film.

As shown in FIG. 11, the present system uses an arrangement which prevents acquisition of undesirable X-rays that originate from other than a newly-deposited film or the substrate. The subject system is provided with an X-ray shield (gate) 50 which is designed to prevent the X-rays of an undesirable origin from being acquired by the X-ray sensor 36. The shield 50 is made from a material which is not transparent to the X-ray material, and thus intercepts these X-rays and prevents the X-ray sensor 36 from processing them. This is an important provision available in the subject apparatus 10 since an amount of remaining materials near the new substrate can be greater than that of the film under deposition.

The subject apparatus is configured to operate in the preferred range of take-off angles of the incident e-beam 32 relative to the surface of the substrate 18 (or the film 20) to bombard a "beam footprint" 52 (area of the electronic beam 32 on the film surface), at which the X-rays originate. The take-off angle 34 (as shown in FIG. 1) is selected in the subject system to be larger than the "angle of total external reflection" of X-rays.

In order to avoid instability when operating in the vicinity of critical angles, the take-off angle 34 in the subject technique is selected to be greater than the critical angles range, i.e., greater than 3 degree as a minimum, and preferably greater than 5 degree.

In addition, in order to facilitate the functionality of the X-ray shield 50, the take-off angle is limited, due to the fact that the large angle requires the larger X-ray shield 50 that can undesirably interfere with the deposition material flux 14. Thus, in an exemplary embodiment, the take-off angle of 10 degrees is used.

In FIG. 11, the electron beam 32 collides with the surface of the substrate 18 (or film 20) to form the beam footprint 52. The X-rays radiate from points 55 of the direct electrons impact within the beam footprint 52. The X-rays 57 radiated from points 55 within the beam footprint 52 are able to pass the shield 50, and are counted by the X-ray sensor 36, while the X-rays 60 generated by the scattered electrons 56 from the surfaces other than the substrate 18 (or film 20), are intercepted by the gate-shield 50.

Substrate supports 54 are used in the system 10. The substrate supports 54 extend away from substrate surface in the Z-direction. Excitation electrons 32 are incident on the substrate 18 (or the film 20) surface and cause useful characteristic X-rays of the substrate (film) elements collected by the X-ray sensor 36. However, some fraction 56 of the energetic electrons 32 is scattered by the substrate 18 (film 20) surface. The scattered electrons 56 can impact the surfaces 58 of the substrate supports 54, and may cause X-ray generation from these surfaces, manifested by spurious X-rays 60 which are undesirable in the subject system since they can alter the intensities of elemental peaks of the film 20 under study, or create additional interfering peaks.

The undesirable X-rays 60 can originate not only from the material of the supports 54, but also from the material layers remaining from previous depositions. X-ray intensities ratios for such remains can be very different from the ones in the film 20 under study, thus causing errors in the film composition computations.

In order to overcome this obstacle, the X-ray gate-shield 50 made of non-transparent X-rays material is employed to prevent undesirable X-rays 60 from being acquired by the X-ray sensor 36. Sizes and location of the gate-shield 50 are selected to intercept X-rays originating from any surface which extends in Z-direction from the substrate (film) surface, and thus is exposed to scattered electrons, for example, the surface 58 of the support elements 54.

For the gate-shield 50 to be able to screen the X-ray sensor 36 from undesirable X-rays 60 which originate from the supports 54, the gate shield extent 62 from the substrate plane has to be sufficiently large. The greater the take-off angle 34, the greater the gate shield extent 62 is required to screen surfaces 58 from the sensor 36 field of view.

On the other hand, the extent 62 cannot be too large. As the gate-shield 50 is located in proximity to the substrate 18 (or film 20), and thus in proximity to the incoming deposition material flux, being expanded in Z-direction, the gate-shield 50 can disturb the incoming flux of the deposition material, and thus can affect the film quality.

With an acceptable maximum gate-shield extent 62 estimated as ~0.3 of film deposition size, the maximum angle between the substrate 18 (or film 20) surface and a line from the support 54 to the edge of the gate-shield 50 is restricted to Arcsine(0.3) or ~17 degree. This requirement leads to a limitation of X-ray sensor angle (take-off angle). It has been concluded that the take-off angle, in the preferred embodiment, shall be smaller than 20 degrees, and most preferred between 4 and 15 degrees. In the exemplary embodiment, the angle of 10 degrees is used.

Width 64 of the gate opening between shields 50 shall be smaller than the minimal distance 66 between the supports 50. In this case, the supports 54 are not visible by the sensor 36 (X-rays originating from the support surfaces 58 are intercepted by the shields 50). For example, for the substrate of 10×10 mm dimensions supported by ~1 mm wide supports 54, the distance 66 is ~8 mm. In this case, an appropriate width 64 of the opening is ~5 mm.

As described in the previous paragraphs, preferred values of the electron beam incidence angle and the X-ray take-off angle, are relatively small. For this reason, the subject method and system may be termed "dynamic low angle X-ray spectrometry".

However some elements of the walls of the deposition vacuum vessel 12 can come into field of view of the X-ray sensor 36. It has been found that the intensity of X-rays from the walls of the chamber 12 is weak since they are located at much larger distance from the substrate 18 than the support elements 54. Thus, they do not contribute significantly to the acquired spectra counts.

Total field of view of the X-ray sensor 36 is restricted by a collimator 100 of the sensor assembly 36, which is presented in FIG. 14 and described in the following paragraphs. However, if necessary, the field of view of the X-ray sensor 36 can be reduced further to minimize the signals originating from the deposition chamber walls.

Additionally, a backdrop screen 68 made of low-X-ray emissivity material (for example, Carbon) can be placed opposite to the sensor 36 to shield the walls of the chamber 12 from field of view of the sensor 36. The screen is located as far as possible from the deposition area in order to minimize the film material accumulation on it.

Films with spatial variation of composition across their surface can also be fabricated by using special deposition setup. The subject system 10 is provided with a mechanism to measure film composition at multiple locations on the film surface, in order to study films properties as a function of position on the film surface.

In the present system, by limiting the area of the X-ray acquisition, spectra from different locations on the film can be acquired. If the composition is intentionally varied, for example, by executing a non-uniform, composition-spread deposition, a "map" of film compositions can be obtained. Spectra are acquired sequentially, one location after another, after each deposition step.

Figure 12A:
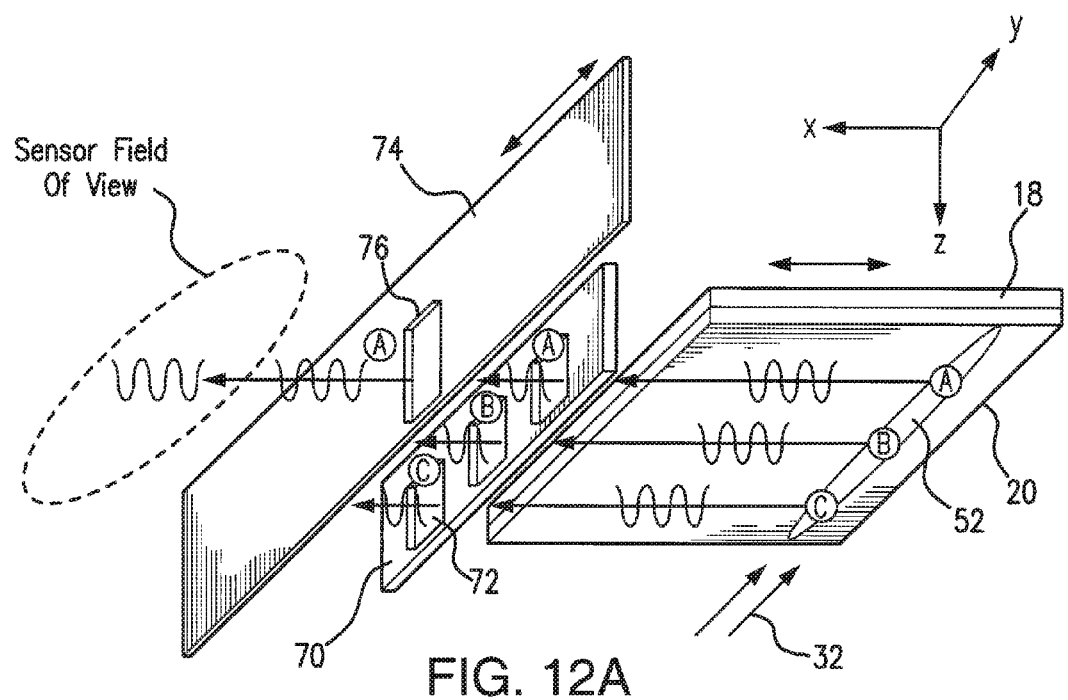
FIGS. 12A-12B are a schematic representations of the subject system configured with the capability of the composition analysis for multiple areas A, B, C of the film under study.
Figure 12B:
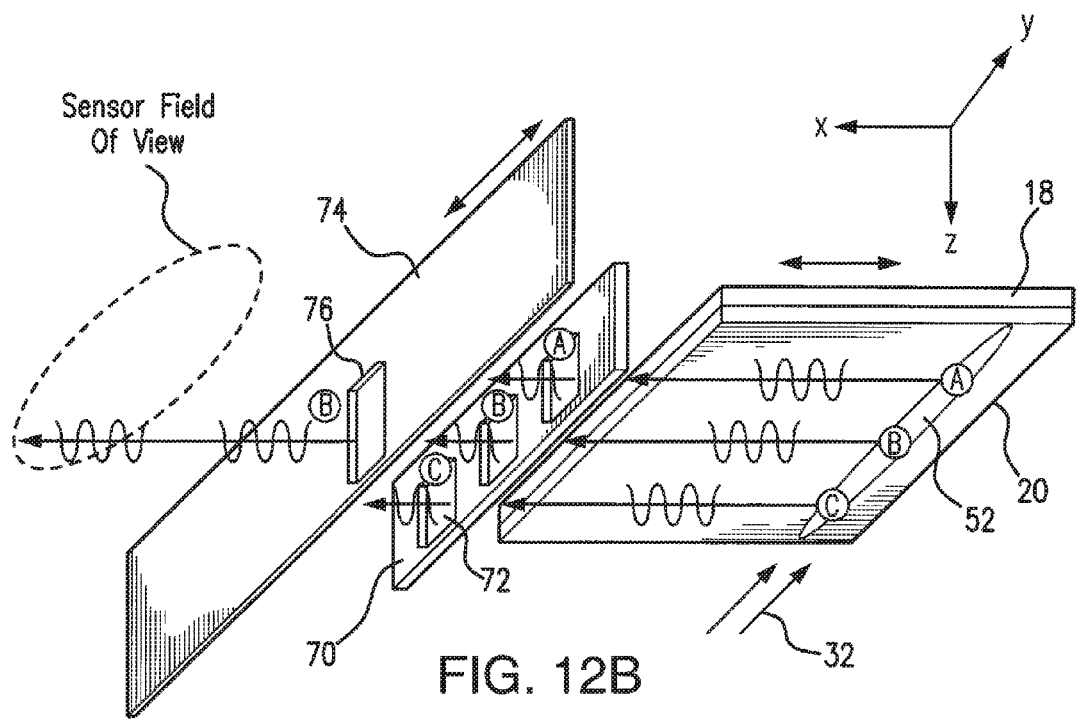

A variety of techniques of changing from one acquisition location to another are envisioned to support obtaining the "map" of compositions in the subject system. For example, an arrangement capable of executing multiple-areas analysis is shown in FIGS. 12A-12B. The same method and algorithm as described in previous paragraphs is applied for the spectra acquisition and the composition determination. The difference is that, after each deposition step (stage), multiple areas on the surface are sequentially interrogated. The setup shown in FIGS. 12A-12B is just an example, and numerous other arrangements are envisioned for relative displacements between the electronic beam, the sensor, screens, etc. to provide the selective acquisition of X-ray spectra from different locations on the film.

Figure 13:
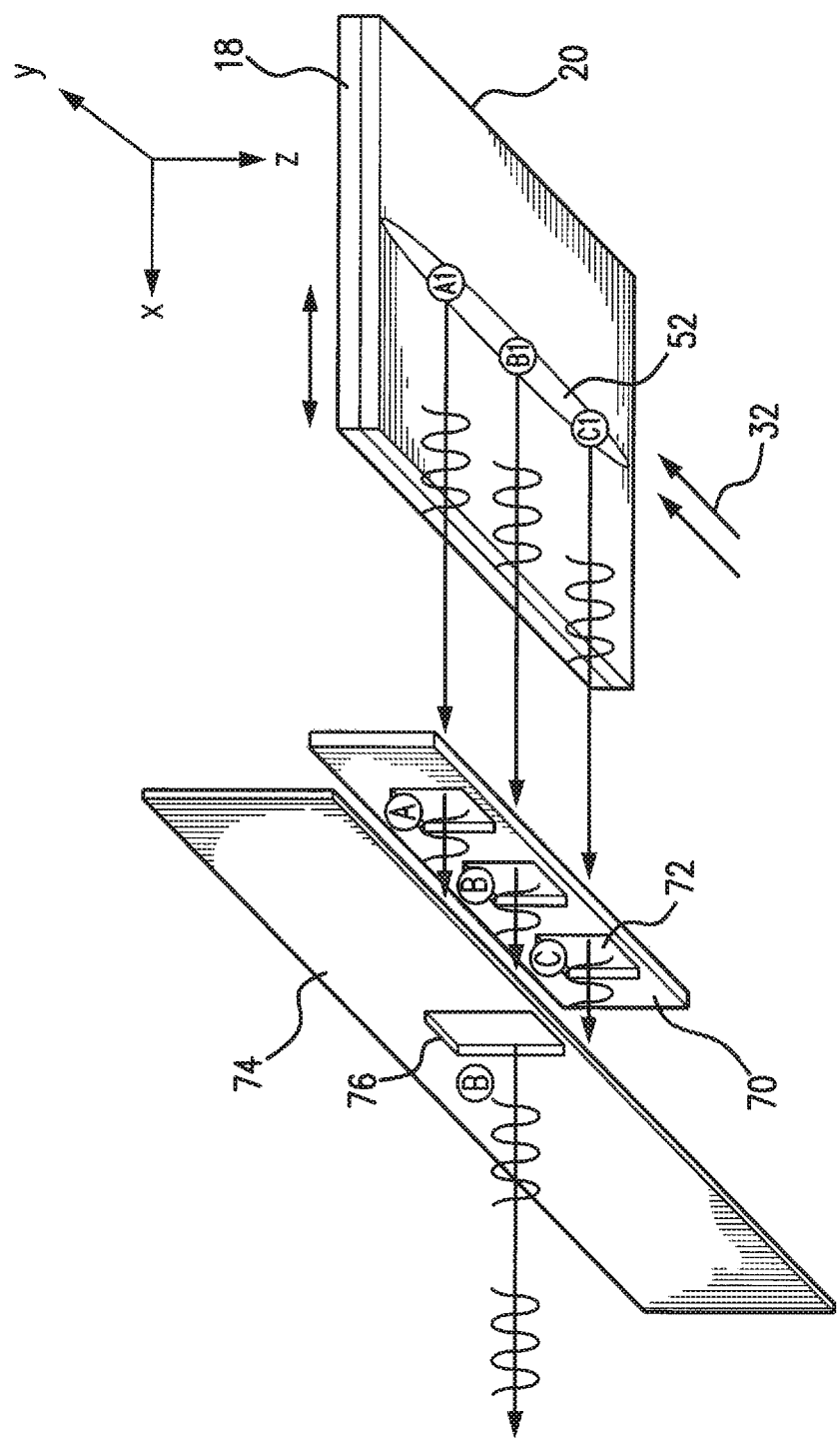
FIG. 13 is a schematic representation of the subject system provided with a mechanism for multi-area "interrogation" of the film surface, for the composition analysis of a set of areas $(A_1, B_1, C_1)$ at different locations along the X-axis.

Referring to FIGS. 12A-12B and 13, the electron beam 32 creates an X-ray emitting area (beam footprint) 52 on the surface of the film 20. To enable, for example, the analysis of the film composition in three locations A, B, C of the footprint 52 on the surface of the film 20, a screen 70 with corresponding windows 72 (A, B, C) is placed in front of the substrate (film 20). The windows 72 define, and spatially separate, X-rays originating from the locations A, B, and C on the surface of the substrate 20.

A selector shield 74 movable in the Y-direction is placed in front of the screen 70. The selector 74 has a window 76 of the size at least equal or greater than the size of each window 72. When the window 76 is aligned with a respective window 72 of interest, X-rays from one of areas A, B, or C of interest aligned with the window 72 can pass to the X-ray sensor 36.

When in position shown in FIG. 12A, i.e., the window 76 is aligned with the window A (on the screen 70), the selector shield 74 allows the passage of radiation from the area A. When the selector shield 74 is shifted to a next Y-position (as shown in FIG. 12B), only radiation from the area B is allowed to pass to the sensor 36. In the similar manner, multiple locations of the film 20 can be interrogated.

Another arrangement for areas "interrogation" is shown in FIG. 13, where the substrate can be displaced relative to the e-beam 32 in X-axis direction. Upon displacing the substrate along X-axis (or displacing the electronic beam 32 relative to the substrate), the sequential interrogation technique for areas $A_1$, $B_1$, $C_1$ displaced along the X-axis relative to the locations A, B, C of FIGS. 12A-12B, may be applied.

The size of the electron beam footprint in Y direction is limited. For the substrates of a size larger than the footprint size, the substrate 18 can be moved in the Y-direction in order to locate the beam footprint in different surface areas.

Figure 14:
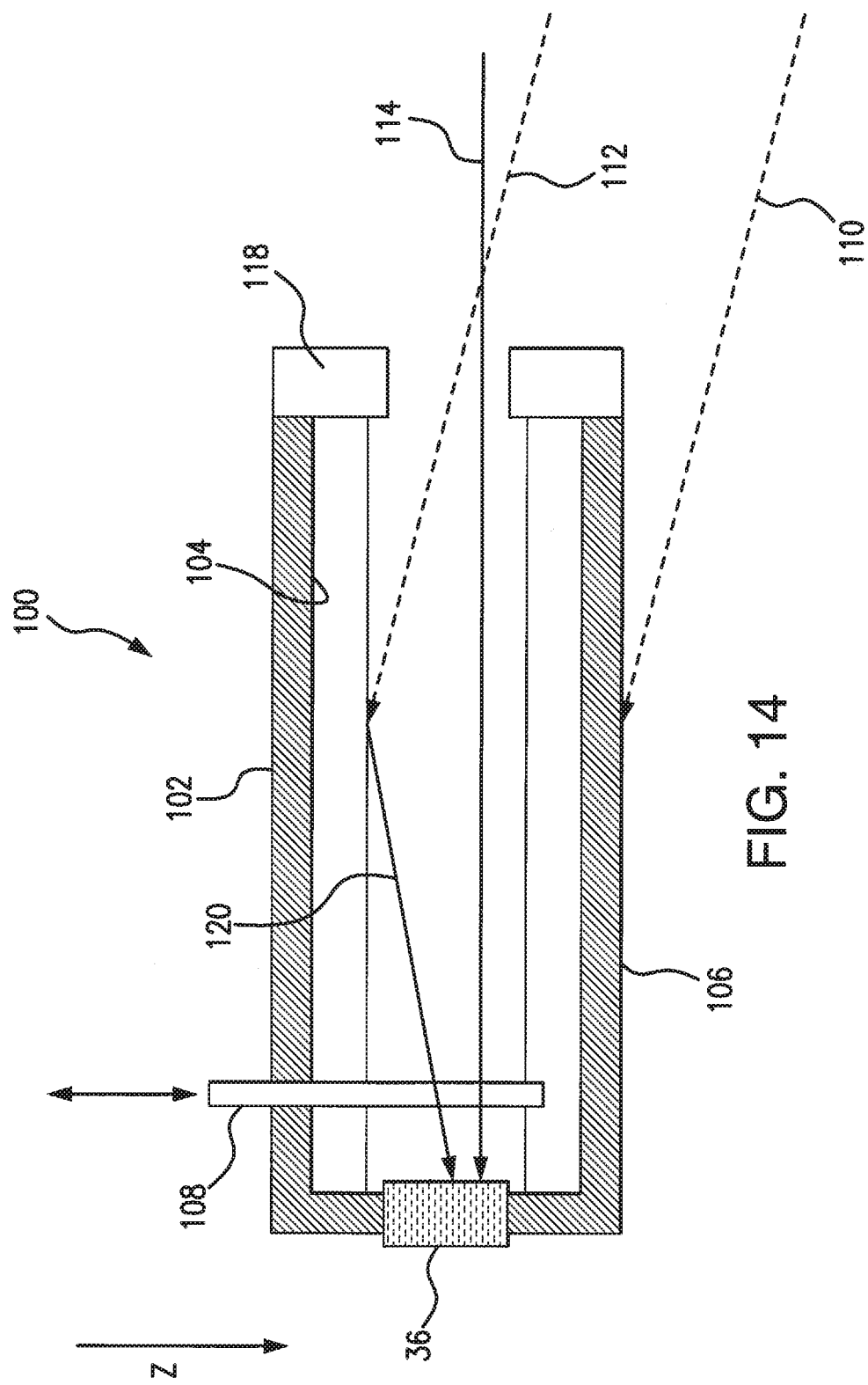
FIG. 14 is a schematic representation of the subject system detailing the collimator assembly attached to the X-ray sensor.

Shown in FIG. 14 is a collimator assembly 100 mounted at the input of the X-ray sensor 36. The function of the collimator assembly 100 is to limit field (angle) of view of the sensor 36. The collimator assembly placed at the input of the sensor 36 is essentially an elongated body of such geometry that X-rays 110 and 112 incident at angles greater than specified angle are intercepted and not allowed to reach the sensor 36. Smaller-angle X-rays 114 are able to pass to the sensor 36.

An outer shroud 102 of the collimator assembly 100 made of X-ray absorbing material (metal) intercepts the rays 110. The insert liner 104 and front aperture 118 of the collimator assembly 100 are made of a material which has a low capability to emit X-rays in a range of interest. The rational for that choice is that some large-incidence angle X-rays 112 can still enter via the collimator aperture 118, and cause a secondary, i.e., fluorescent X-ray emission 120 from the liner material 104. Due to the close location of the inner surface of the liner to the sensor 36, an intensity of such an undesirable signal 120 can be considerable. In order to minimize the effect on the acquired spectrum, the material of the liner 104 and the front aperture 118 are selected based on the requirement for its X-ray emission to be below an energy range of interest. For compositional analysis of elements with atomic numbers greater than 11 (Na), the PEEK material that consists mostly of Carbon, Oxygen, and Fluorine can be chosen for the elements 104 and 118.

In order to maximize the efficiency of the sensor 36 for analyzing the areas about the size of the sensor 36, the size of the aperture 118 has also to be about the size of the sensor. The length of the collimator 100 preferred embodiment is chosen to be such that the entire electron beam footprint on the substrate surface is within the field-of-view of the sensor 36 from any point of the sensor, in the embodiment, total angle of field of view is ~6 degrees.

The subject system further includes a sacrificial sensor protector 108 placed in front of the input window of the sensor 36. The protector 58 is made of a thin plate (film) of a polymer material transparent to the X-rays of interest. The protector 58 intercepts the material occasional entering the collimator assembly due to the scattering during the film deposition. The protector is removable and replaceable and eliminates possible contamination of the sensor window.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of the elements may be reversed or interposed, all without departing from the spirit or scope of the invention as defined in the appended claims.

What is claimed is:

1. A method for in-situ determination of chemical composition of films during a deposition process, comprising:
    (a) positioning an underlying structure in a deposition chamber, and bombarding a predetermined area of said underlying structure with an electron beam incident on a surface of said underlying structure at a first predetermined angle;
    (b) operatively coupling an X-ray spectrum acquisition sub-system to said surface of said underlying structure;
    (c) acquiring, by said X-ray spectrum acquisition subsystem, a "zero-film" X-ray spectrum produced by said underlying structure upon exposure to said electron beam prior to deposition of a film of interest on said underlying structure;
    (d) initiating a deposition process to deposit a material containing at least two elements A and B for the film of interest on said underlying structure, wherein said deposition process is performed in a plurality of sequential predetermined stages, each said stage for deposition of a partial thickness of said film of interest; for each of said stages,
    (e) acquiring, by said X-ray spectrum acquisition system, a respective X-ray spectrum emitted by said film of interest in said each stage of the deposition process;
    (f) analyzing said respective X-ray spectrum relative to said "zero-film" X-ray spectrum to determine at least two X-ray peaks present thereat, each of said at least two X-ray peaks corresponding to a respective element of said at least two elements A and B of said material of said film of interest;
    (g) computing intensities $J_A(N)$ and $J_B(N)$ of said at least two peaks, where N is a parameter corresponding to a thickness of said film of interest formed in said each stage of the deposition process;
    (h) computing a ratio $R_{A/B}(N)$ between said intensities $J_A(N)$ and $J_B(N)$;
    (i) computing a ratio $R_{A/B}(0)$ for a virtual film of substantially zero thickness for said at least two elements A and B by applying a best fitting function across said $J_A(N)$, $J_B(N)$, and $R_{A/B}(N)$ in said each stage of the deposition process; and
    (j) computing a ratio of concentrations $C_A/C_B$ for said at least two elements A and B as a product of the value of said $R_{A/B}(0)$ and a relative sensitivity number $K_{A/B}$ representing a constant instrumental factor.

2. The method of claim 1, further including the step of: repeating said steps (e)-(j) for said plurality of stages of the deposition process.

3. The method of claim 1, wherein said underlying structure includes a substrate for deposition of said film of interest or a film-on-substrate structure underlying said film of interest.

4. The method of claim 2, further comprising:
    subsequent to said step (c), determining "zero-film" correction spectrum data corresponding to contribution of unwanted residual elements, and
    in said step (f), performing a correction routine by applying said correction spectrum data to said X-ray spectrum to subtract X-ray counts produced by the unwanted residual elements for said respective X-ray spectrum acquired during said each stage of the deposition process.

5. The method of claim 2, further comprising the step of:
    inserting a predetermined time interval between subsequent said stages of the deposition process if a speed of the spectrum acquisition is lower than the speed of increase of the film of interest during said deposition process.

6. The method of claim 1, further comprising the steps of:
    prior to said step (j), determining a relative sensitivity factor $K_{A/B}$ for at least said two elements A and B,
    said relative sensitivity factor $K_{A/B}$ being determined through the steps of:
    depositing a calibration film containing said elements A and B, and applying said steps (f)-(j) to measuring said $R_{A/B}(0)$ of said calibration film, and
    determining the composition $C_A/C_B$ of the calibration film by an independent technique, and
    subsequently to determination of the $R_{A/B}(0)$ and $C_A/C_B$ for the calibration film, calculating said $K_{A/B}=(C_A/C_B)/R_{A/B}(0)$.

7. The method of claim 6, further comprising the steps of:
    wherein said at least two elements A and B include at least elements A, B, and C,
    determining said relative sensitivity factor for a number of various pairs of elements, including $K_{A/B}$, $K_{A/C}$, $K_{B/C}$, and storing in a database,
    wherein $K_{A/B}=K_{A/C}/K_{B/C}$.

8. The method of claim 1, wherein said parameter corresponding to a thickness of said film of interest includes a number of laser pulses or a time of deposition.

9. The method of claim 1, wherein said material of the film of interest includes at least elements A, B, and C, the method further comprising:
    for said each stage of the deposition technique,
    in said step (g), computing values of peak intensities $J_A(N)$, $J_B(N)$, $J_C(N)$ of elemental lines corresponding to said elements A, B, and C, respectively,
    graphing said intensities ($J_A(N)$, $J_B(N)$, $J_C(N)$) of each elemental peak against said thickness related parameter N,
    computing ratios $R_{A/C}(N)$, $R_{B/C}(N)$, of intensities $J_A(N)$, $J_B(N)$, of each said element A, B to intensity $J_C(N)$ of the element C, and graphing said ratios against said thickness related parameter N,
    curve-fitting said J(N) and R(N) for said elements A, B, and C across the graphed $J_A(N)$, $J_B(N)$, and $J_C(N)$, and $R_{A/C}(N)$, $R_{B/C}(N)$, and
    in each said step (i), for each element A and B, fitting results of the curve-fitting down to respective $R_{A/C}(0)$ and $R_{B/C}(0)$.

10. The method of claim 1, further comprising the steps of:
    subsequent to said step (g), determining a thickness of said film of interest as a function of reduction of the intensity Js of at least one peak corresponding to an element of a material of said underlying structure through the steps of:

computing Js(N)/Js(0) intensity of said at least one peak normalized to the intensity Js(0) found in said "zero-film" X-ray spectrum after the film thickness related parameter N has been applied during at least one stage of the deposition procedure, calibrating said normalized intensity against a calibration film having a known thickness for a given pair of substrate element-film material, and applying said calibration to the obtained normalized Js(N)/Js(0) to calculate the film of interest thickness in real-time.

11. A system for in-situ determination of chemical composition of films during a deposition process, comprising:

a deposition chamber;

a substrate positioned within said deposition chamber;

a source of deposition material for deposition on a surface of said substrate to grow a film of interest;

a source of electron beam directed to be incident on the surface of said film of interest at a first predetermined angle;

at least one X-ray sensor positioned at a second predetermined angle relative to said surface to collect X-rays emitted therefrom;

a spectra acquisition sub-system operatively coupled to said at least one X-ray sensor and configured to form a respective X-ray spectrum from X-ray counts collected by said at least one X-ray sensor during each of a plurality of stages of the deposition process;

a spectra processing sub-system operatively coupled to said X-ray spectra acquisition sub-system and configured to:

analyze said respective X-ray spectrum to determine at least two X-ray peaks present thereat, each of said at least two X-ray peaks corresponding to a respective element of at least two elements A and B of said deposition material of said film of interest, compute intensities $J_A(N)$ and $J_B(N)$ of said at least two peaks, where N is a parameter corresponding to a thickness of said film of interest formed during said each stage of the deposition process, and compute a ratio $R_{A/B}(N)$ of said intensities $J_A(N)$ and $J_B(N)$, a composition computation sub-system operatively coupled to said spectra processing sub-system and configured for:

computing a ratio $R_{A/B}(0)$ for a virtual film of substantially zero thickness for said at least two elements A and B by applying a best fitting function across said $J_A(N)$, $J_B(N)$ and $R_{A/B}(N)$ in said at least one stage, and computing a ratio of concentrations $C_A/C_B$ for said at least two elements A and B as a product of the value of said $R_{A/B}(0)$ and a relative sensitivity factor $K_{A/B}$, representing an instrumental factor constant; and a control unit operatively coupled to said source of electron beam source of deposition material, X-ray sensor, and said X-ray acquisition, spectra processing and composition computing sub-systems to control said deposition process, said X-ray emission, said first and second predetermined angles, and said X-ray acquisition and processing routines, and to acquire said X-ray spectra for a plurality of subsequent deposition process stages, and to process said X-ray spectra for each said deposition stage integrally until the deposition process is completed.

12. The system of claim 11, wherein said first predetermined angle between the electron beam and the surface of said underlying structure or said film of interest is within the appropriate range between 3 and 45 degrees.

13. The system of claim 11, wherein said X-ray spectrum acquisition sub-system includes said at least one X-ray sensor positioned at an angle relative to the surface of the underlying structure or the film of interest ranging from 3 to 20 degrees.

14. The system of claim 11, further comprising:

a user interface operatively coupled to said control unit and said X-ray spectra processing and composition computing sub-systems.

15. The system of claim 11, further comprising gate shields disposed between the substrate or the film of interest and said at least one X-ray sensor and positioned at a selected first distance therebetween and a selected second distance relative to the surface of said substrate or said film of interest to shield said at least one X-ray sensor from detection of unwanted emitted X-rays.

16. The system of claim 11, further comprising backdrop screen made of a low X-ray emissivity material and positioning in said deposition chamber at a side of said substrate opposite to said at least one X-ray sensor to shield said X-ray sensor from unwanted X-ray emitted from the deposition chamber walls.

17. The system of claim 11, further including an interrogation mechanism for acquiring X-ray spectra from a plurality of areas on the surface of said film of interest, said interrogation mechanism including:

a screen formed with a plurality of screen windows and disposed between said film of interest and said at least one X-ray sensor, and a selector shield formed with a selector window and disposed between said screen and said at least one X-ray sensor, wherein a relative disposition between said screen and selector shield is controlled to align said selector window with a respective one of said screen windows corresponding to an area of interest on said film of interest.

18. The system of claim 17, wherein said film of interest is controllably displaceable relative to the electron beam.

19. The system of claim 11, further including a collimator assembly mounted at an input of said at least one X-ray sensor configured to control the field-of-view thereof.

20. The system of claim 19, wherein said collimator assembly includes a protector structure positioned in front of said X-ray sensor to eliminate contamination of the window of the X-ray sensor.

* * * * *